(12) United States Patent
Ootani et al.

(10) Patent No.: US 8,114,347 B2
(45) Date of Patent: Feb. 14, 2012

(54) PIPETTE CHIP SUPPLY DEVICE, SAMPLE ANALYZING APPARATUS, PIPETTE CHIP SUPPLY METHOD AND SAMPLE ANALYZING METHOD

(75) Inventors: Toshihiro Ootani, Kobe (JP); Kazuya Fukuda, Kobe (JP); Kazunori Mototsu, Kobe (JP); Toshikatsu Fukuju, Kobe (JP); Masayuki Nakagawa, Kako-gun (JP)

(73) Assignee: Sysmex Corporation, Kobe-Shi (JP)

( * ) Notice: Subject to any disclaimer, the term of this patent is extended or adjusted under 35 U.S.C. 154(b) by 1220 days.

(21) Appl. No.: 11/641,849

(22) Filed: Dec. 20, 2006

(65) Prior Publication Data

US 2007/0148042 A1 Jun. 28, 2007

(30) Foreign Application Priority Data

Dec. 22, 2005 (JP) .................................. 2005-368973
Dec. 27, 2005 (JP) .................................. 2005-375179

(51) Int. Cl.
*G01N 35/00* (2006.01)
*B65G 47/14* (2006.01)
(52) U.S. Cl. ............... 422/63; 422/500; 436/55; 221/1; 221/171
(58) Field of Classification Search .............. 422/62, 422/99, 100, 102, 104, 105, 107, 116, 564, 422/933, 526, 500; 221/1, 9, 12–13, 156, 221/157, 161–163, 167, 171; 436/55
See application file for complete search history.

(56) References Cited

U.S. PATENT DOCUMENTS

| 3,870,194 | A | * | 3/1975 | Taylor ........................... 221/160 |
| 5,114,740 | A | * | 5/1992 | Plate et al. .................... 427/533 |
| 5,740,006 | A | * | 4/1998 | Larkin .......................... 361/213 |
| 5,836,437 | A | * | 11/1998 | Saito et al. .................... 198/396 |
| 5,853,079 | A | * | 12/1998 | Ito et al. ......................... 198/395 |
| 2003/0047418 | A1 | * | 3/2003 | Okada et al. ............... 198/459.1 |

FOREIGN PATENT DOCUMENTS

| JP | H6-16328 U | 3/1994 |
| JP | H06-33872 | 6/1994 |
| JP | H7-000833 A | 1/1995 |
| JP | 8-244957 A | 9/1996 |
| JP | H08-233830 | 9/1996 |
| JP | H09-002643 | 1/1997 |
| JP | H9-072922 A | 3/1997 |
| JP | 2000-016570 A | 1/2000 |
| JP | 2000-19182 A | 1/2000 |
| JP | 2000-311797 A | 11/2000 |

OTHER PUBLICATIONS

Japanese Patent Office, "Office Communication," issued in connection with Japanese Patent Application No. 2005-375179, dated May 19, 2011.

* cited by examiner

*Primary Examiner* — Jill Warden
*Assistant Examiner* — Cedric Chan
(74) *Attorney, Agent, or Firm* — Sughrue Mion, PLLC

(57) ABSTRACT

A pipette chip supply device for supplying a pipette chip for suctioning liquid, the pipette chip supply device comprising: a chip accommodating section for accommodating pipette chips; a conveying section for conveying the pipette chips supplied from the chip accommodating section; and a static eliminator for removing electrification charge of the pipette chips.

25 Claims, 23 Drawing Sheets

[Fig. 1]
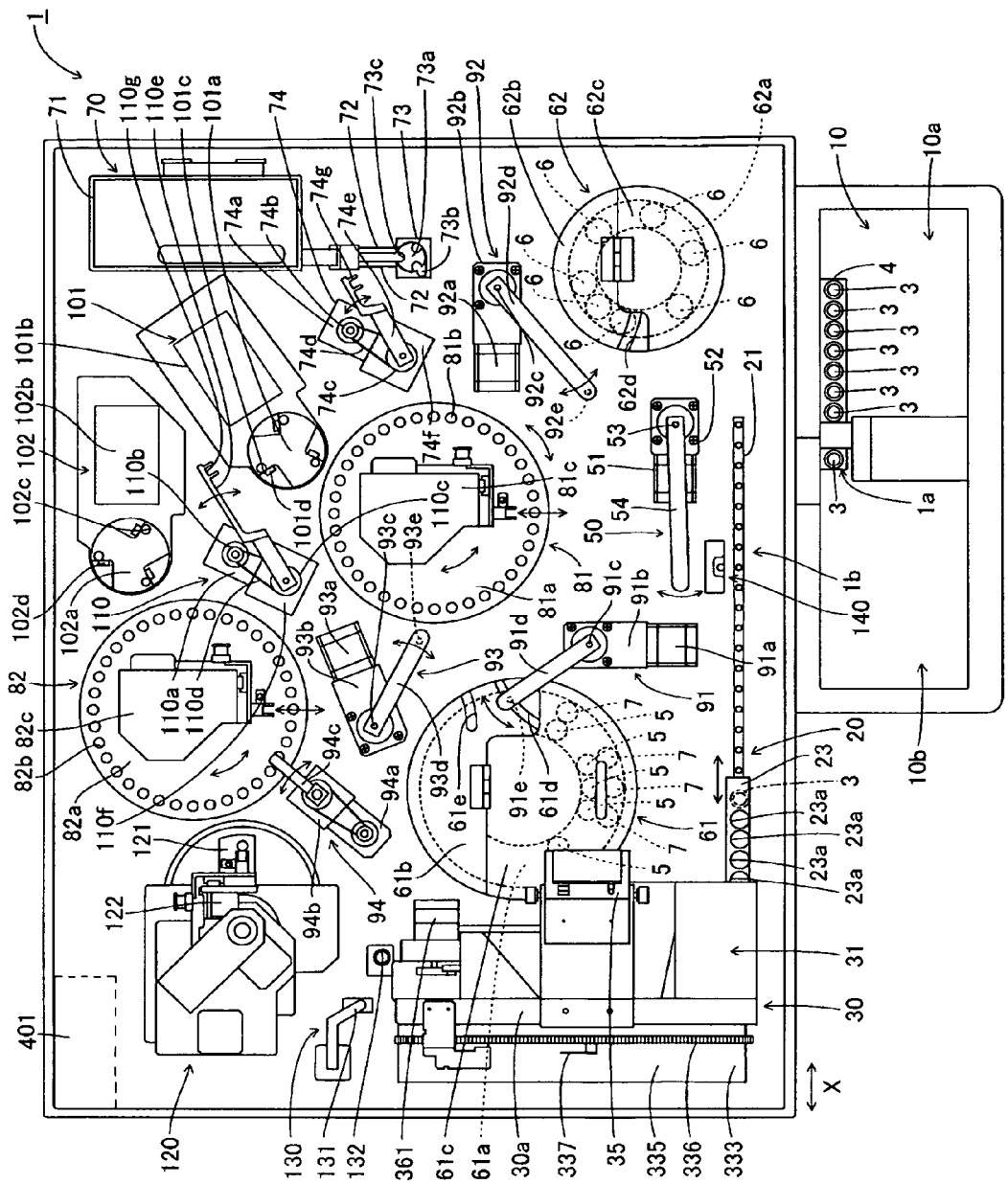

[Fig. 2]
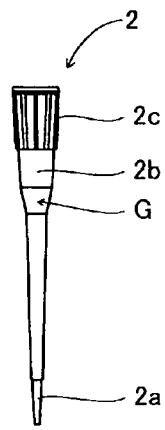
[Fig. 3]
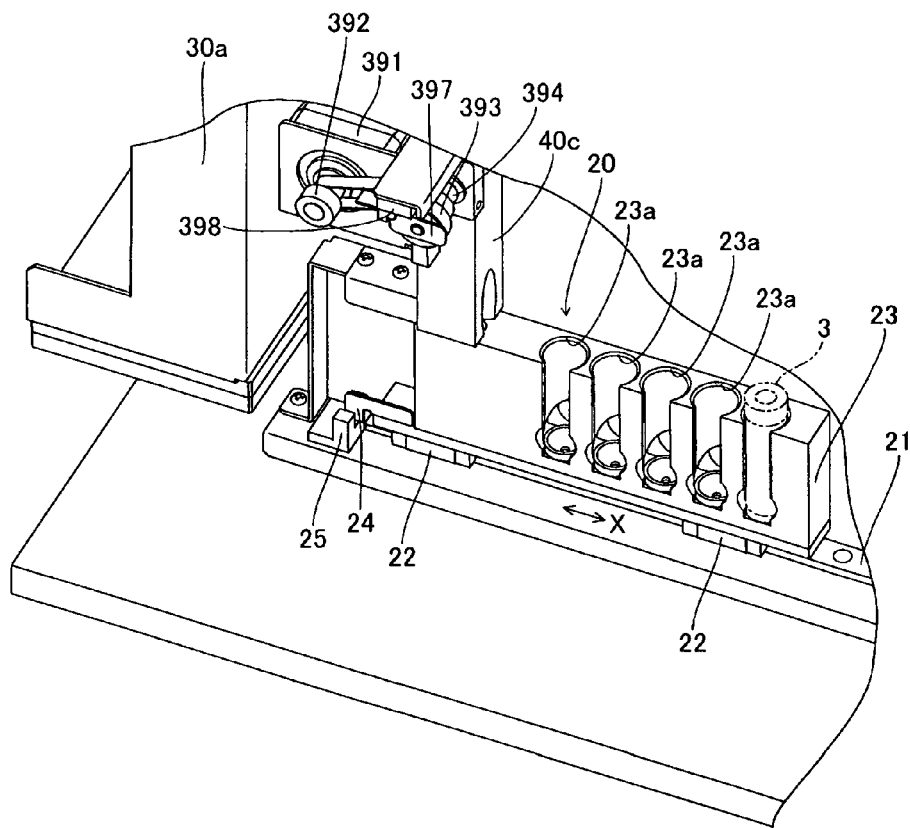

[Fig. 4]
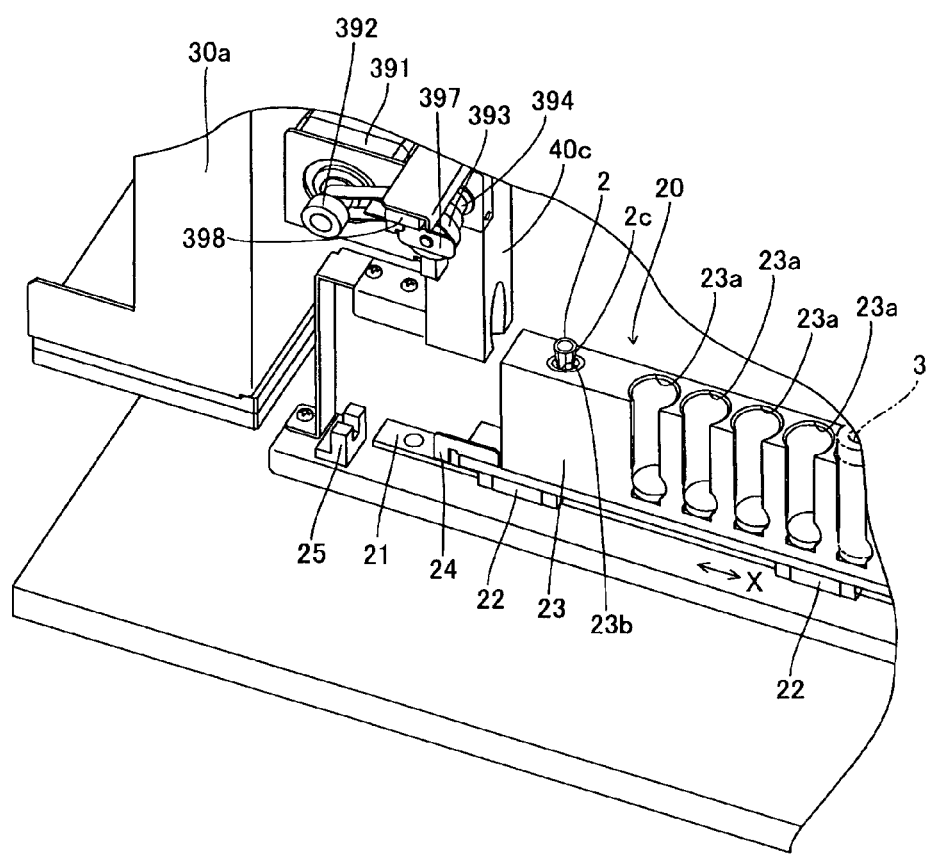

[Fig. 5]
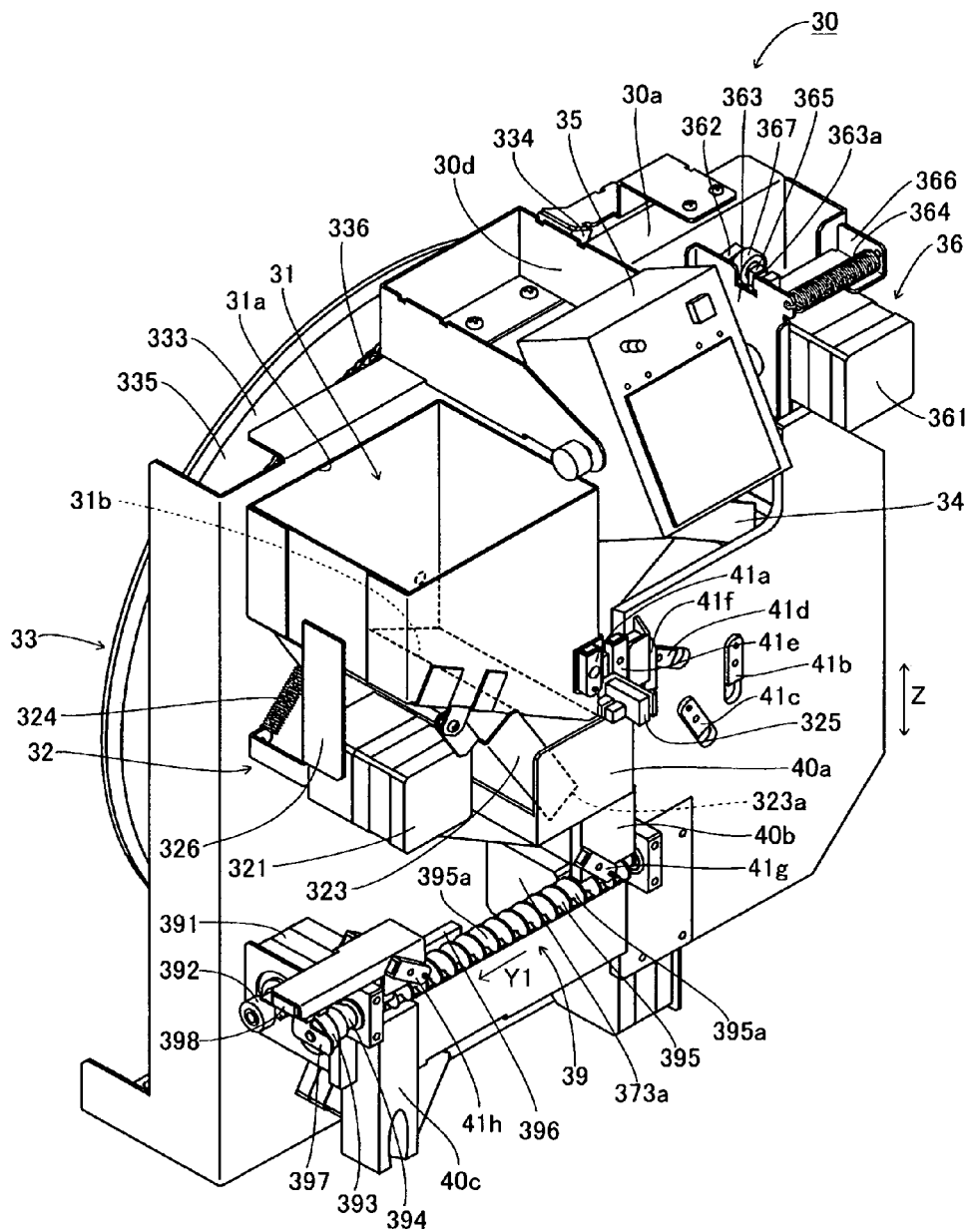

[Fig. 6]
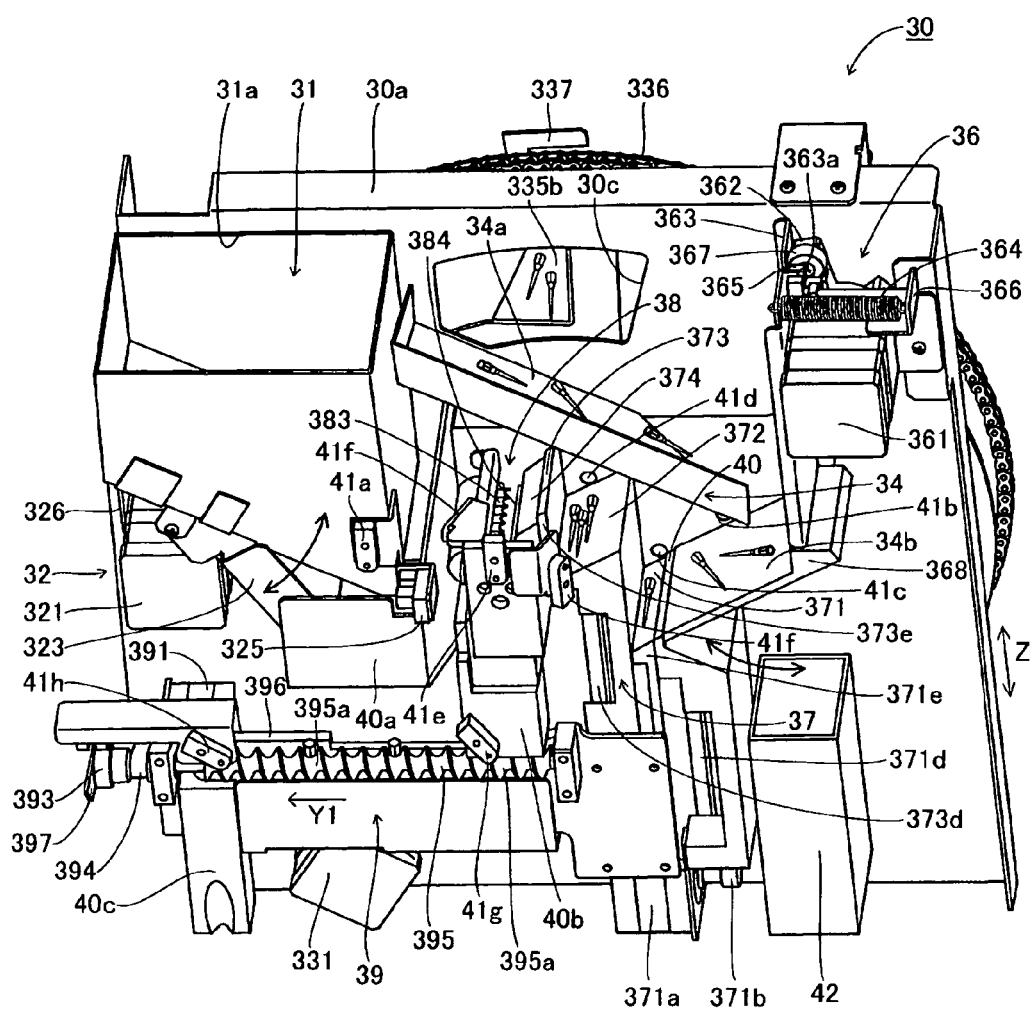

[Fig. 7]
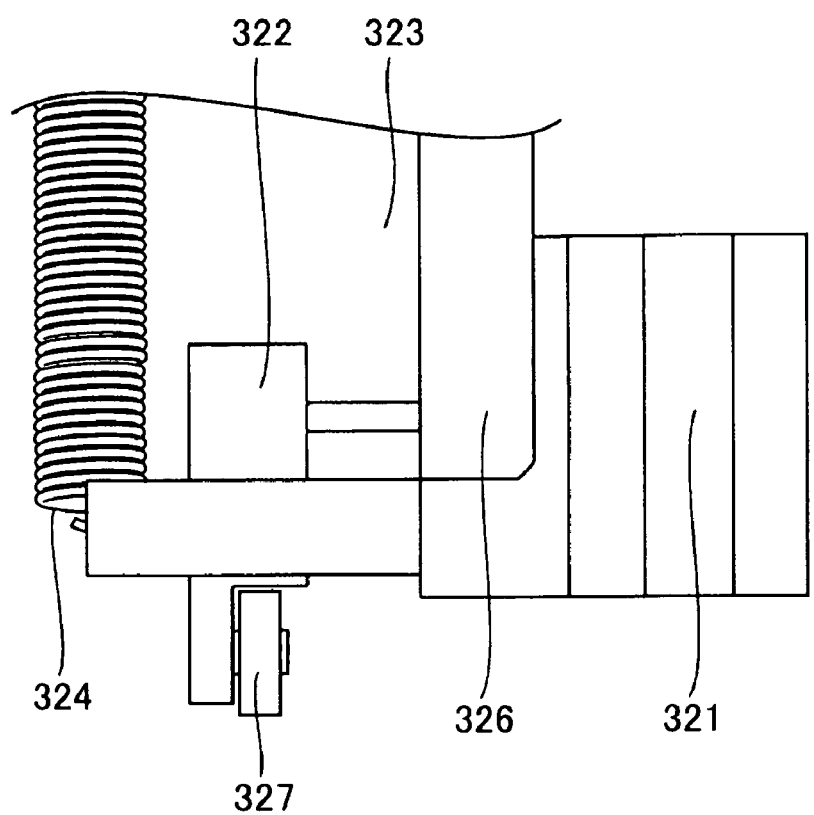

[Fig. 8]
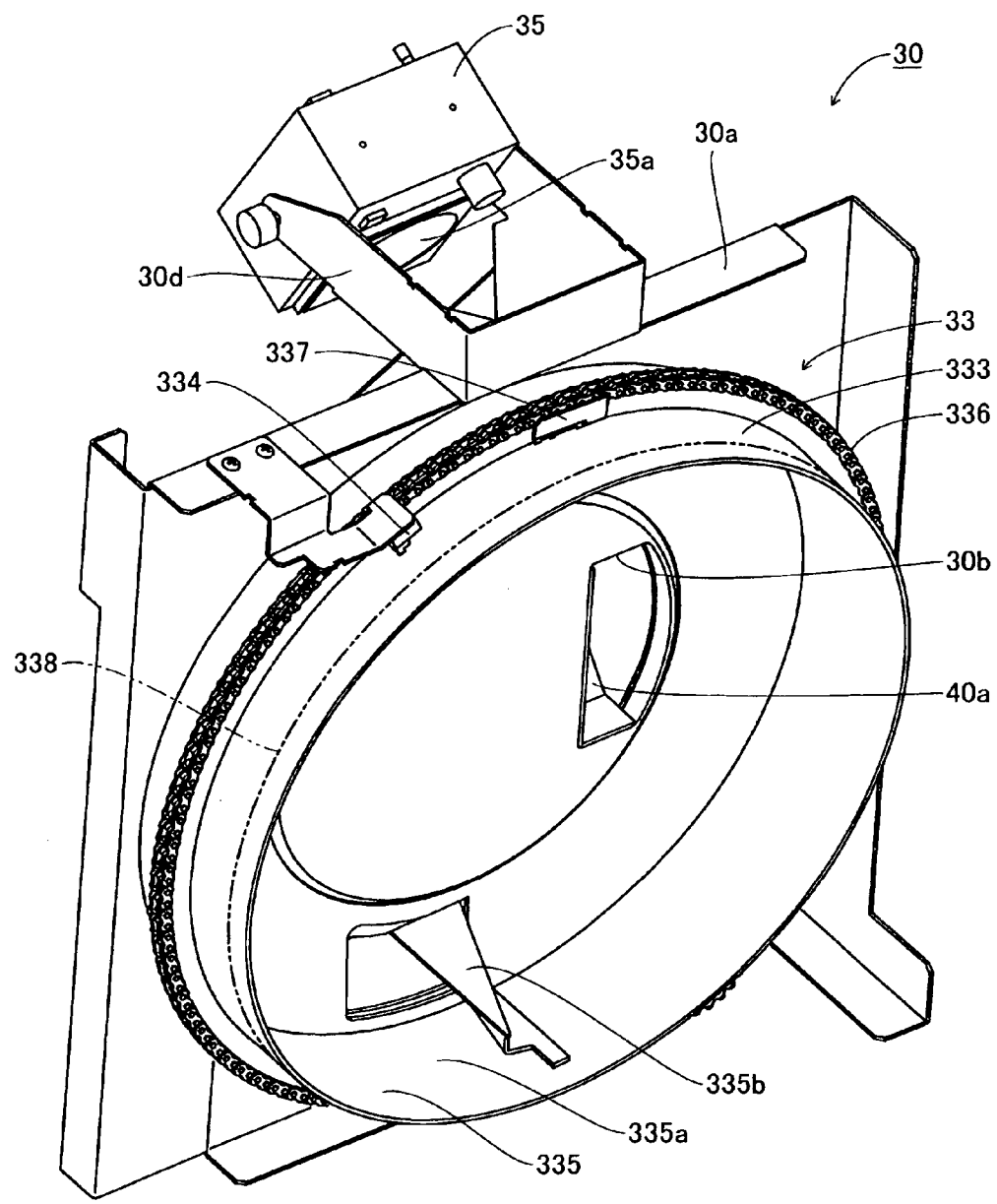

[Fig. 9]
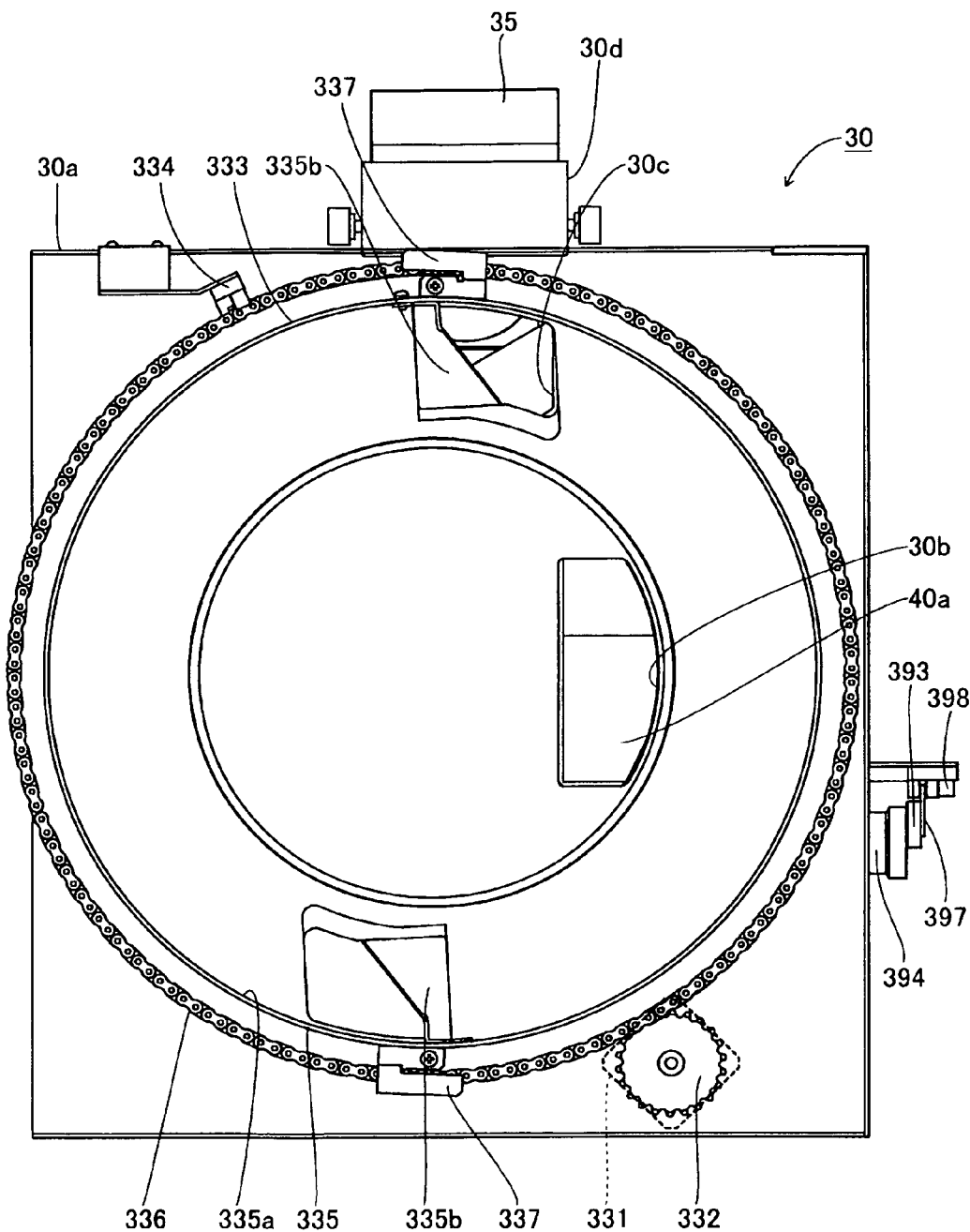

[Fig. 10]
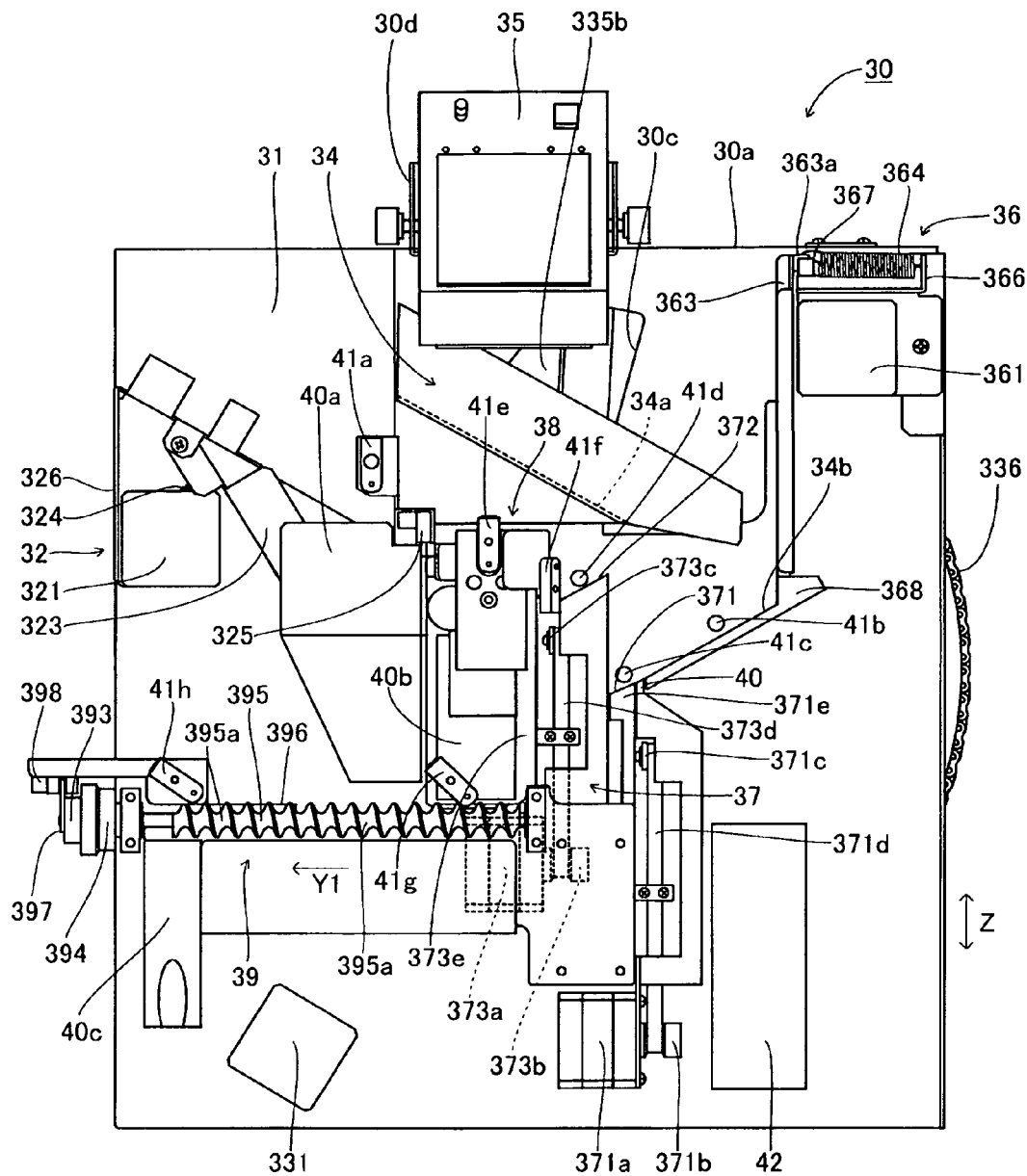

[Fig. 11]
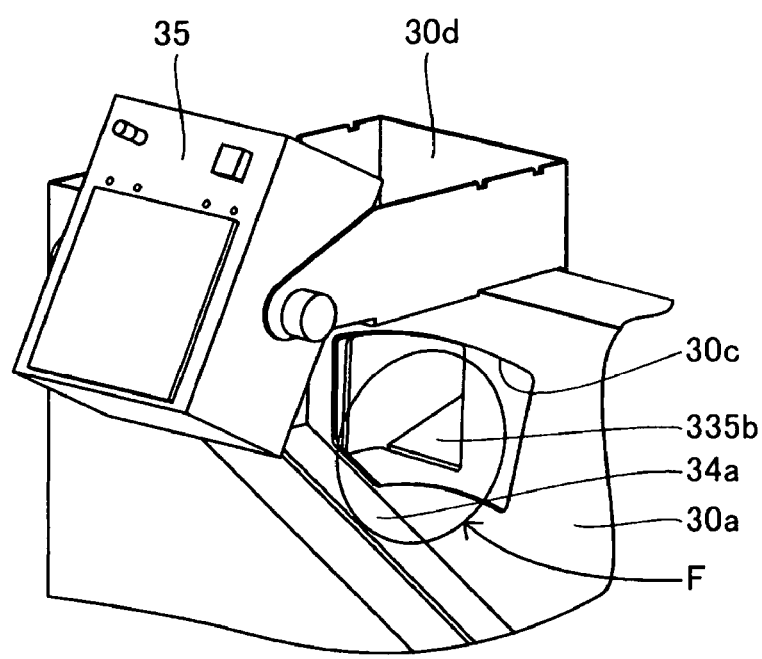

[Fig. 12]
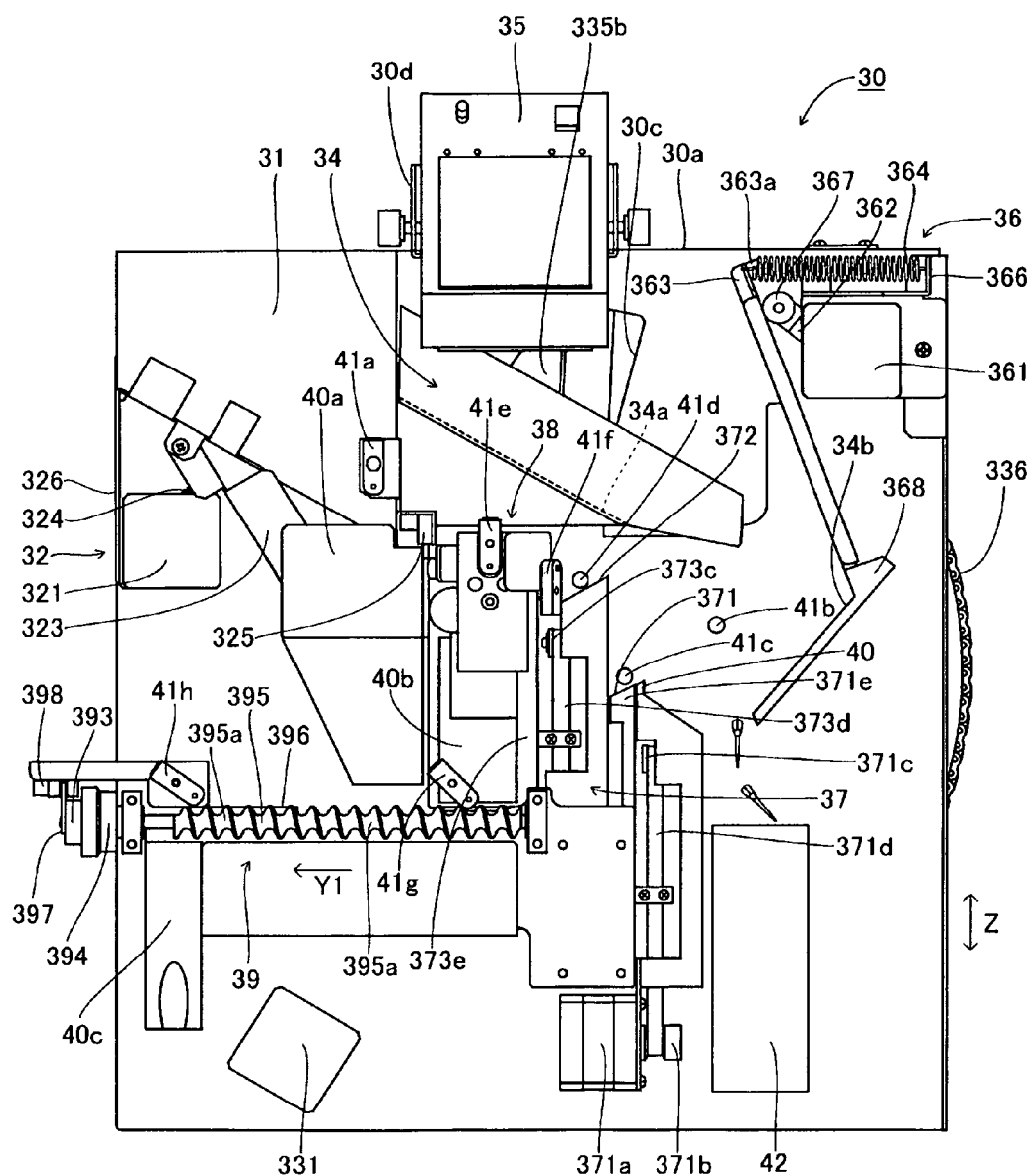

[Fig. 13]
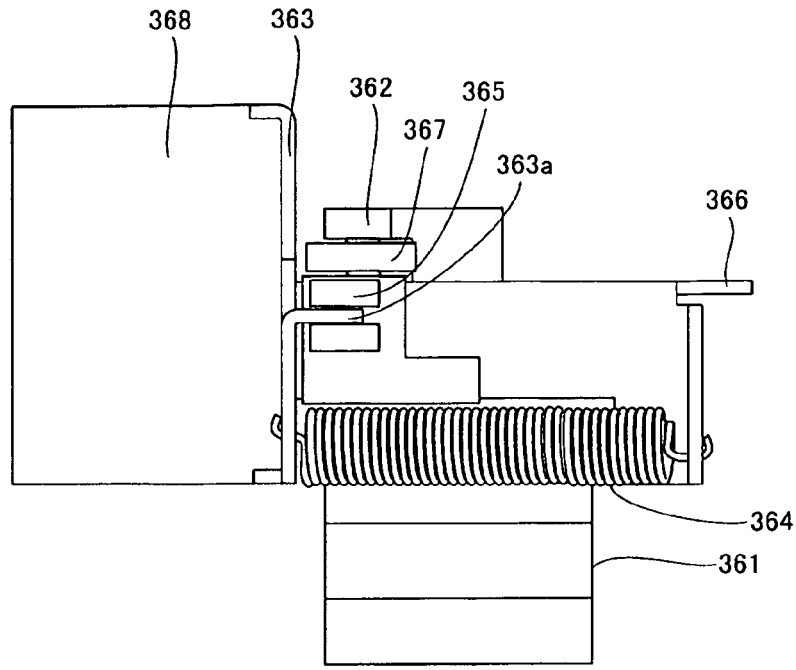
[Fig. 14]
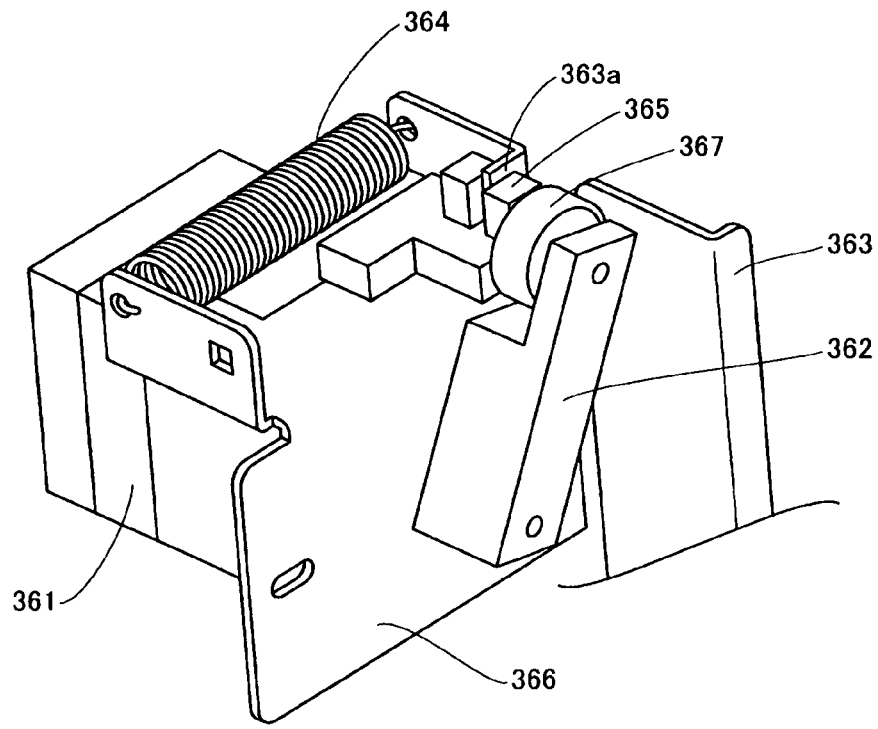

[Fig. 15]
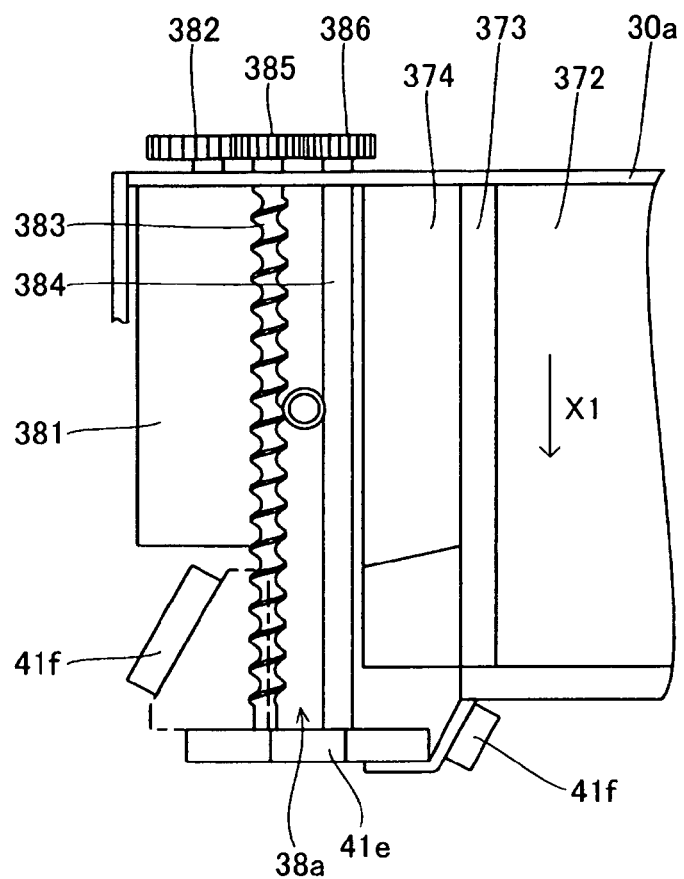
[Fig. 16]
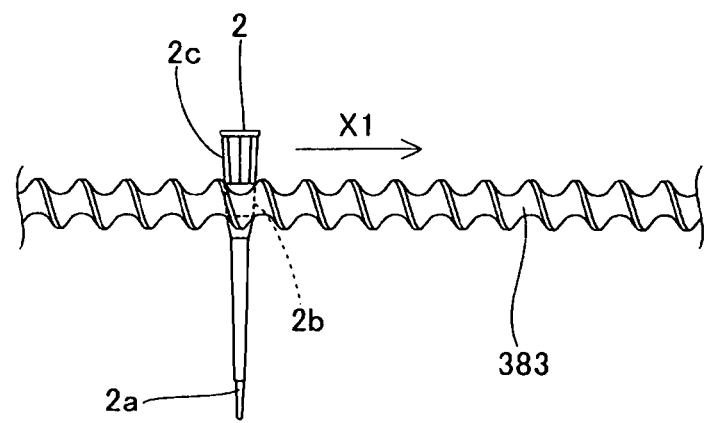

[Fig. 17]
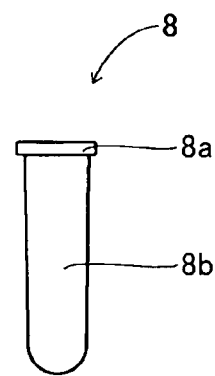
[Fig. 18]
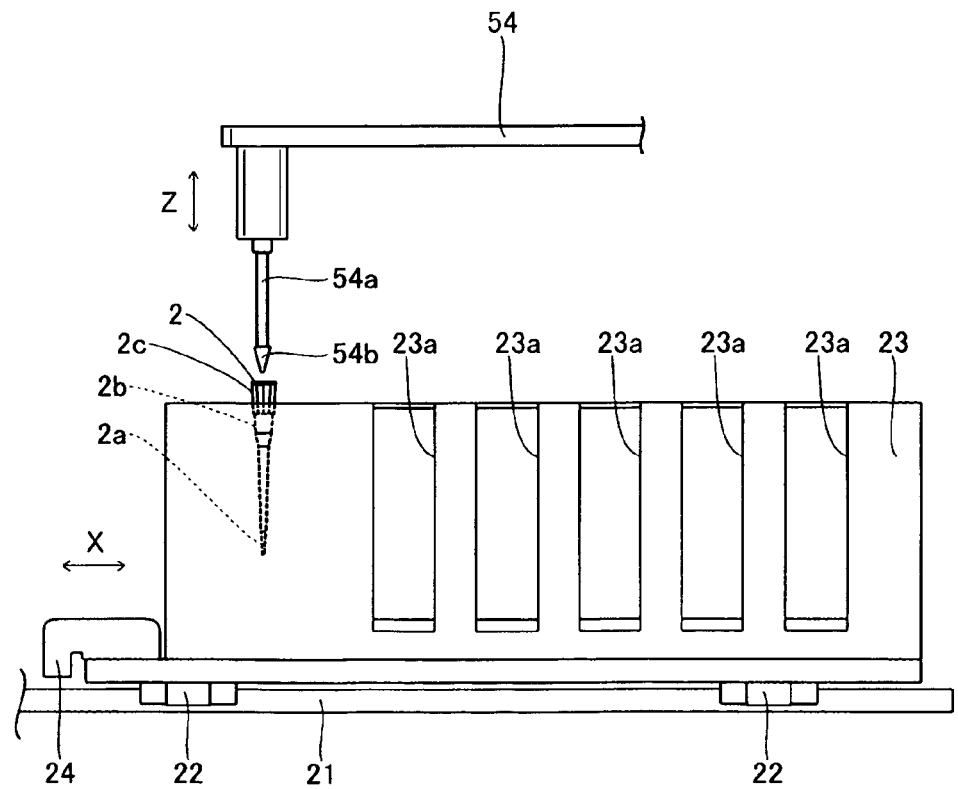

[Fig. 19]
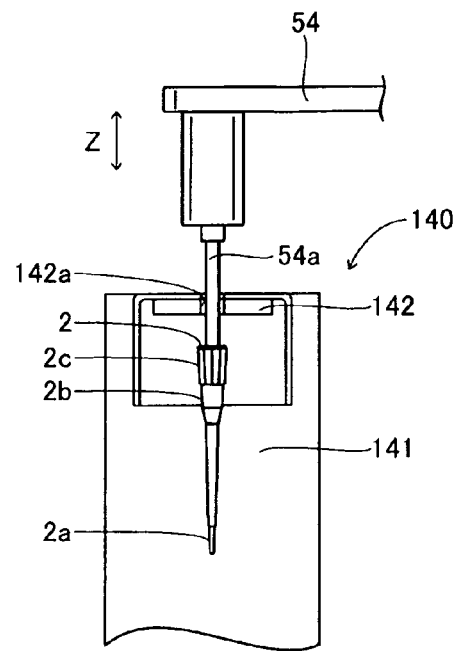
[Fig. 20]
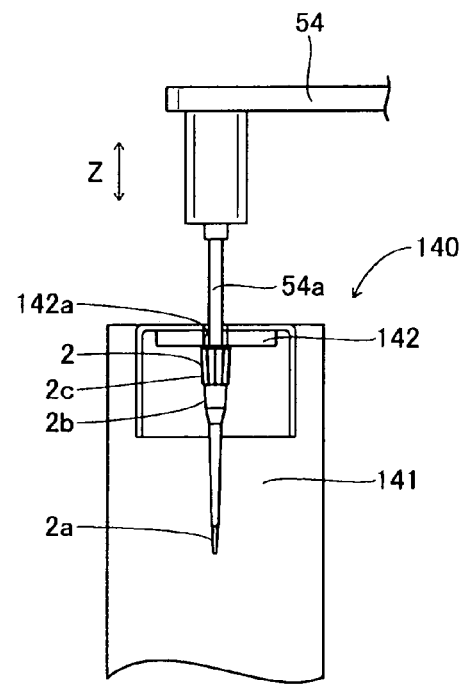

[Fig. 21]
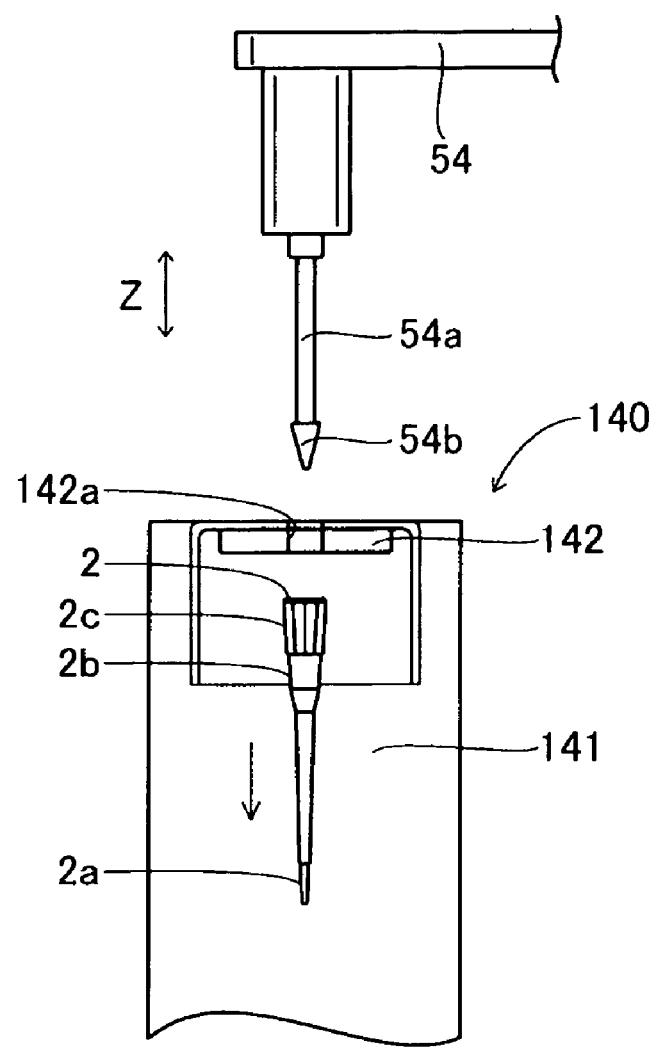

[Fig. 22]
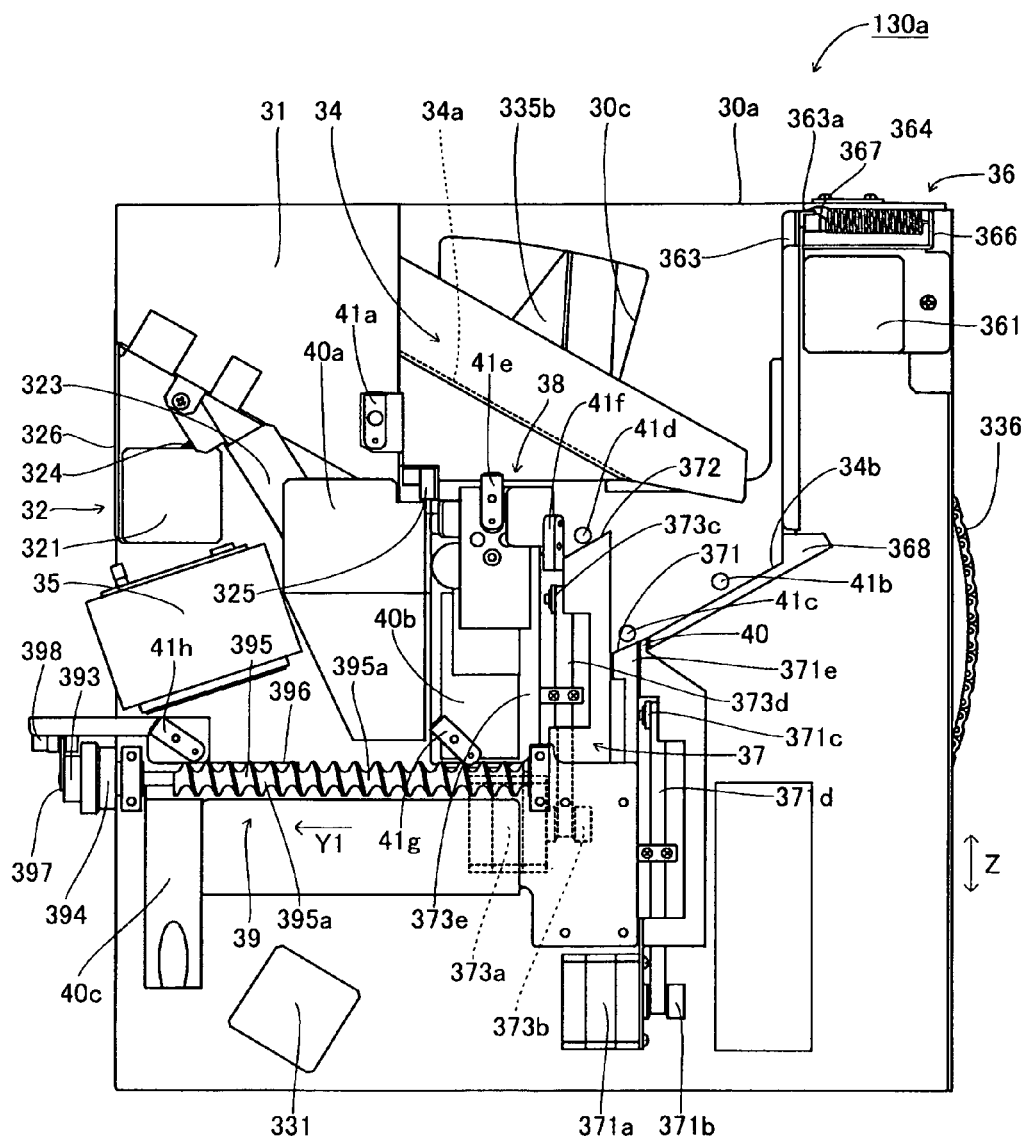

[Fig. 23]
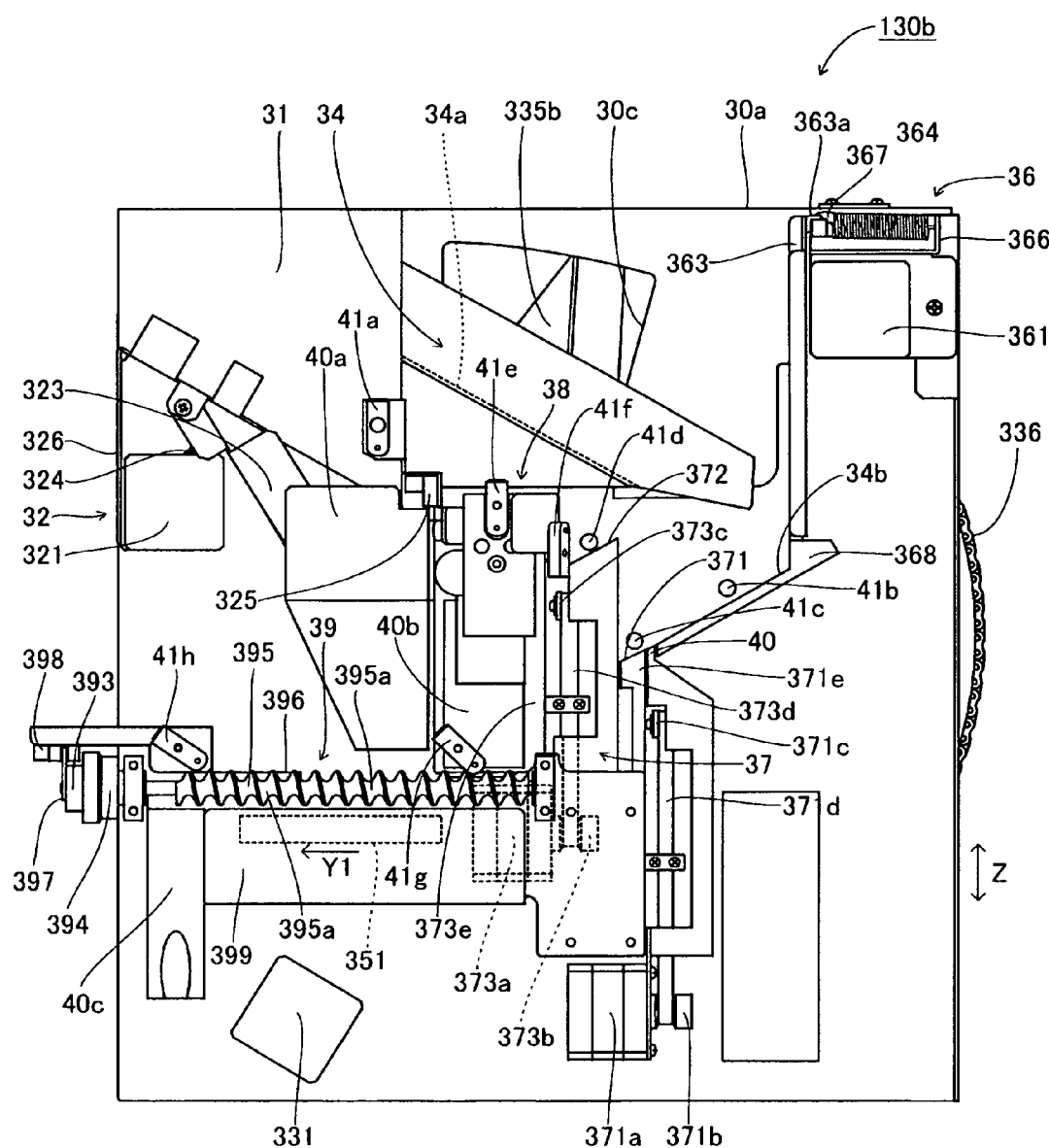

[Fig. 24]
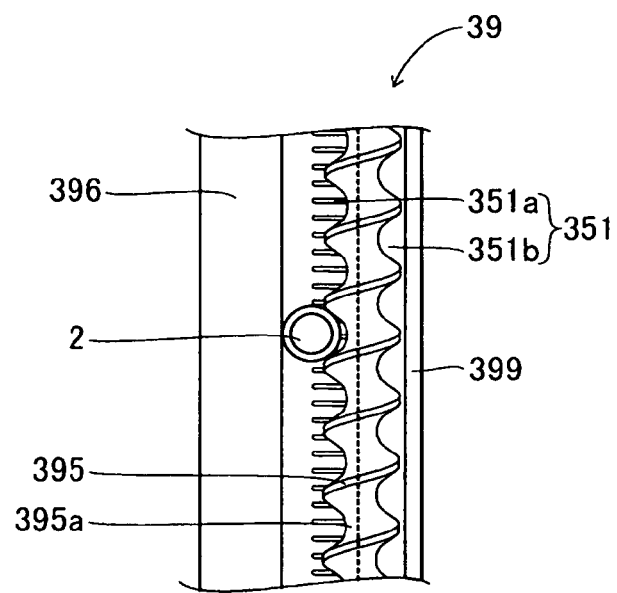
[Fig. 25]
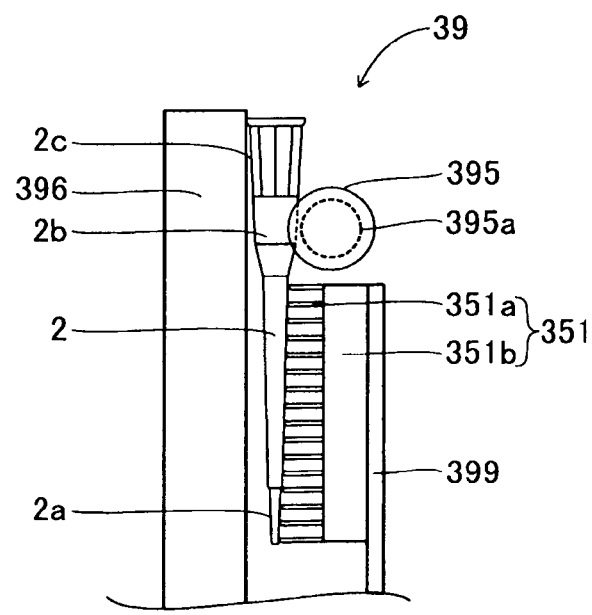

[Fig. 26]
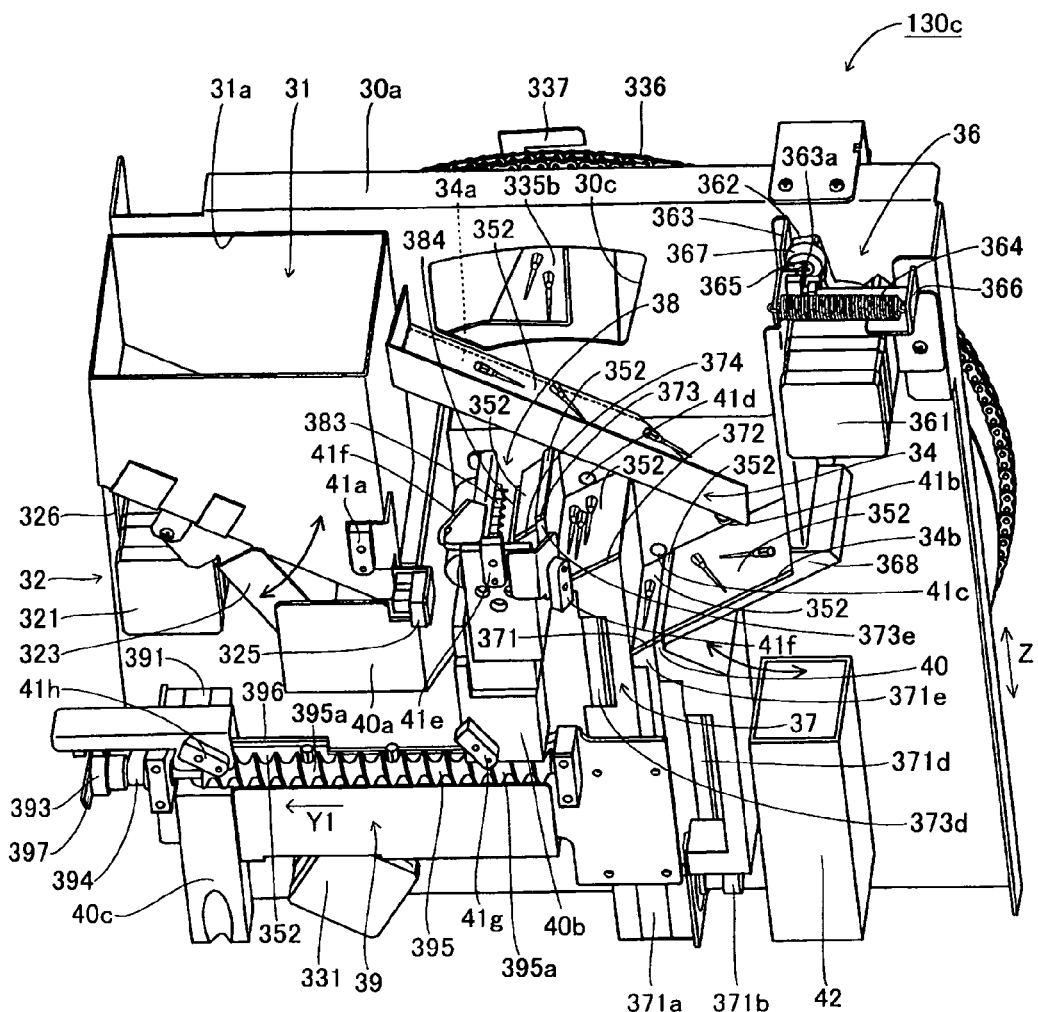

[Fig. 27]
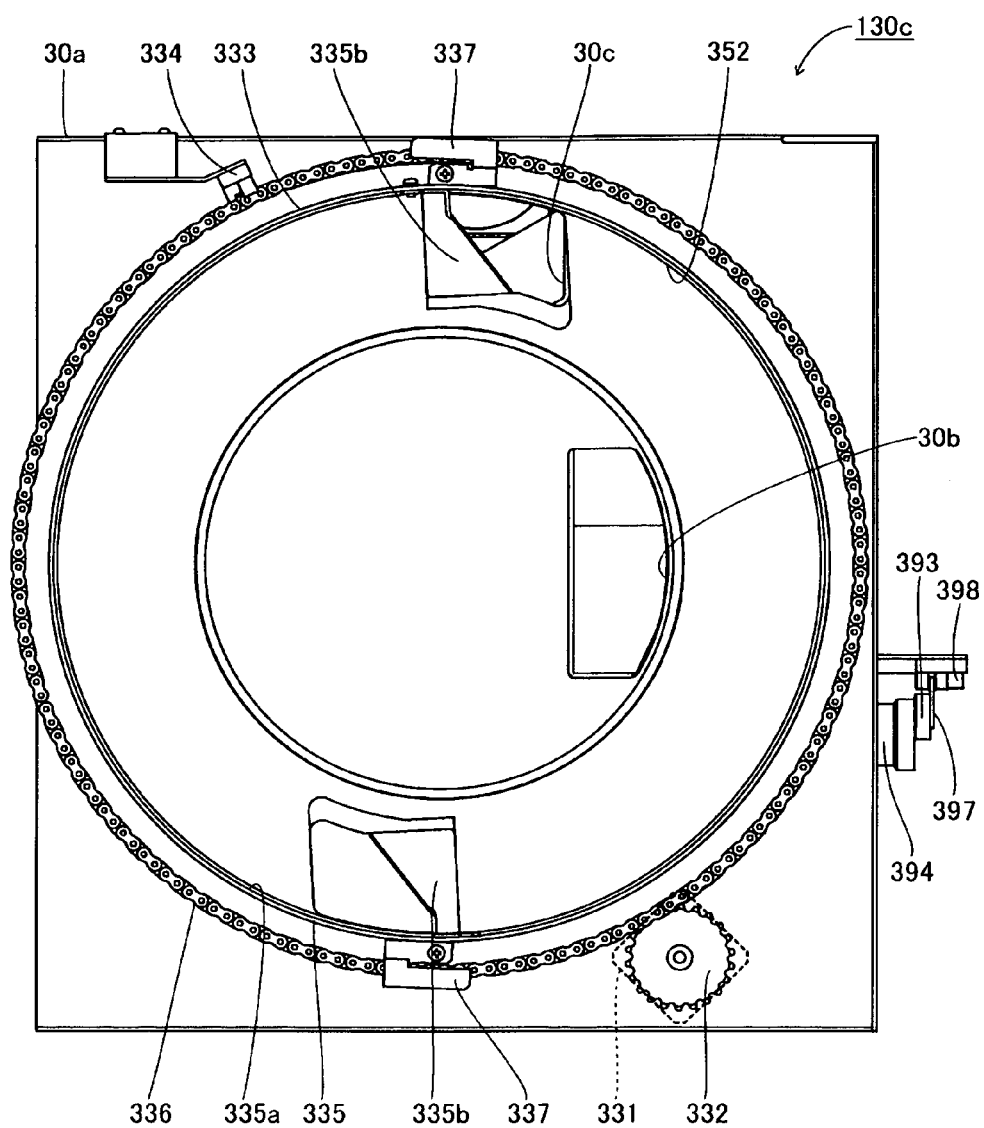

[Fig. 28]
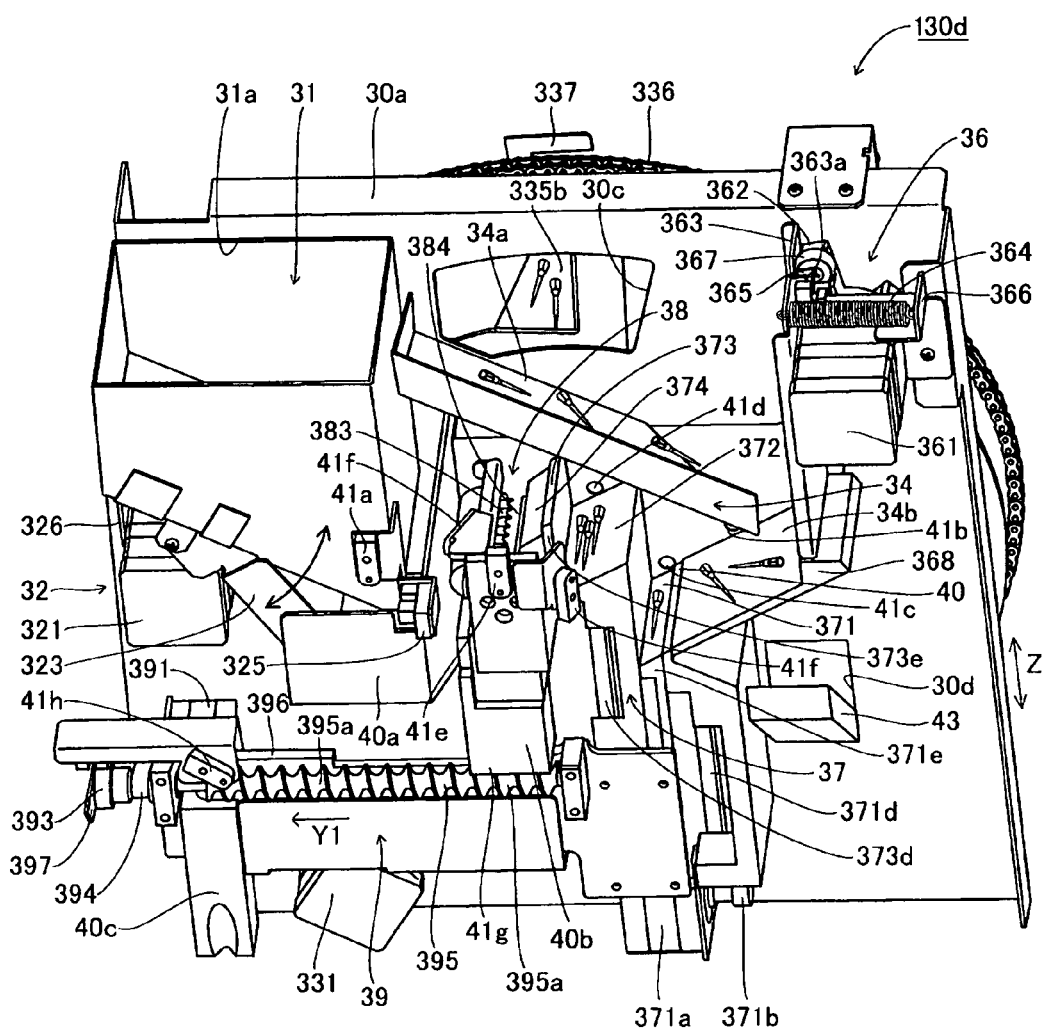

[Fig. 29]
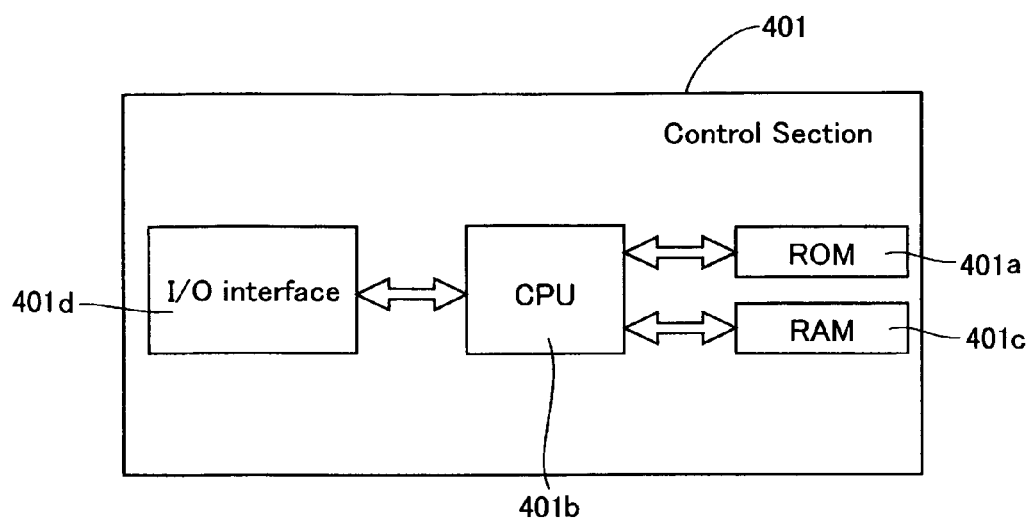

PIPETTE CHIP SUPPLY DEVICE, SAMPLE ANALYZING APPARATUS, PIPETTE CHIP SUPPLY METHOD AND SAMPLE ANALYZING METHOD

BACKGROUND OF THE INVENTION

1. Field of the Invention

The present invention relates to pipette chip supply devices, sample analyzing apparatus, pipette chip supply methods, and sample analyzing methods, in particular, to a pipette chip supply device equipped with a conveying section for conveying a pipette chip, a sample analyzing apparatus, a pipette chip supply method, and a sample analyzing method.

2. Background

Conventionally, an analyzing device removably attached with a disposal-type pipette chip at the distal end of the dispensing nozzle for preventing pollution is known as an analyzing device (specimen analyzing device) equipped with a dispensing nozzle (suction part) for suctioning and discharging liquid such as specimen, reagent and the like.

Such analyzing device generally includes a pipette supply device for supplying a pipette chip to the dispensing nozzle one at a time so as to continuously perform the dispensing task. Various component supply devices have been conventionally proposed as a device for supplying components such as pipette chip (see e.g., Japanese Laid-Open Patent Publication No. 8-244957). A component supply device in which a plurality of components are accommodated in a hopper, and the component is conveyed one at a time by stirring the components accommodated in the hopper is disclosed in Japanese Laid-Open Patent Publication No. 8-244957.

However, the following problems arise when using the component supply device disclosed in Japanese Laid-Open Patent Publication No. 8-244957 as the pipette chip supply device. Static electricity occurs at the pipette chip due to friction between the pipette chips since the plurality of components (pipette chips) accommodated in the hopper are stirred. Thus, the charged pipette chips tend to attach to the supply path of the pipette chip, the pipette chips may attach to each other, and sorting of the pipette chips one by one becomes difficult. Furthermore, if the pipette chips are charged even after the pipette chips are sorted one by one, the pipette chips may attach to the supply path of the pipette chips, the pipette chips may attach to each other, and the supplying of the pipette chip to the dispensing nozzle (suction part) one at a time becomes difficult.

Conventionally, a pipette chip supply device for conveying upward the plurality of pipette chips accommodated in a stocker by a bucket conveyor, guiding the conveyed pipette chips to the hopper from above the bucket conveyor through a shoot (conveying path), and thereafter, conveying the pipette chips in the hopper by means of a conveying rail is known (see e.g., Japanese Laid-Open Patent Publication No. 2000-19182).

However, the pipette chips sometimes accumulate in the shoot and the hopper at the path extending from the shoot (conveying path) to the hopper in the pipette chip supply device disclosed in Japanese Laid-Open Patent Publication No. 2000-19182. In this case, the pipette chips conveyed by the bucket conveyor sequentially accumulate, and the pipette chips may not be conveyed.

SUMMARY OF THE INVENTION

The scope of the present invention is defined solely by the appended claims, and is not affected to any degree by the statements within this summary.

A pipette chip supply device according to a first aspect of the present invention is a pipette chip supply device for supplying a pipette chip for suctioning liquid, the pipette chip supply device comprising: a chip accommodating section for accommodating pipette chips; a conveying section for conveying the pipette chips supplied from the chip accommodating section; and a static eliminator for removing electrification charge of the pipette chips.

A pipette chip supply device according to a second aspect of the present invention is a pipette chip supply device for supplying a pipette chip for suctioning liquid, the pipette chip supply device comprising: a chip accommodating section for accommodating the pipette chips and supplying the pipette chips; a conveying path for conveying the pipette chips supplied from the chip accommodating section; a detector for detecting the accumulation of the pipette chips in the conveying path; and a discharging section for discharging the accumulated pipette chips of the conveying path based on the detection of the accumulation by the detector.

A pipette chip supply device according to a third aspect of the present invention is a pipette chip supply device for supplying a pipette chip for suctioning liquid, the pipette chip supply device comprising: a chip accommodating section for accommodating pipette chips; a sending part for supplying pipette chips accommodated in the chip accommodating section; a conveying path for conveying the pipette chips sent from the sending part; a supply section for supplying one by one the pipette chips received from the conveying path; and a sending controller for controlling the sending part whether the sending part send the pipette chips to the conveying path or not.

A pipette chip supply device according to a fourth aspect of the present invention is a pipette chip supply device for supplying a pipette chip for suctioning liquid; the pipette chip supply device comprising: a chip accommodating section for accommodating pipette chips; a sending part for supplying pipette chips accommodated from the chip accommodating section; a sorter for sorting one by one the pipette chips sent from the sending part a transfer section for transferring the pipette chips so that the distal end of the sorted pipette chips faces downward; a first chip detector for detecting whether the pipette chip is supplied from the sorter to the transfer section or not; a second chip detector for detecting whether the pipette chip is discharged from the transfer section or not; and a controller for controlling the sorter so as to sort the pipette chips based on the first and second chip detected results.

A pipette chip supplying method according to a fifth aspect of the present invention is a pipette chip supply method for supplying a pipette chip for suctioning liquid; the method comprising the steps of: sending pipette chips accommodated in a chip accommodating section to a conveying section; conveying the pipette chips sent from the chip accommodating section by the conveying section; and removing electrification charge of the pipette chips positioned at the chip accommodating section or the conveying section.

A sample analyzing method according to a sixth aspect of the present invention is a sample analyzing method, the method comprising the steps of: sending pipette chips accommodated in a chip accommodating section to a conveying section; conveying the pipette chips sent from the chip accommodating section by the conveying section; removing electrification charge of the pipette chips positioned at the chip accommodating section or the conveying section; attaching the pipette chip supplied from the conveying section to a suction part; suctioning a sample by the suction part; and analyzing the sample suctioned by the suction part.

BRIEF DESCRIPTION OF THE DRAWINGS

The invention, together with objects and advantages thereof, may best be understood by reference to the following description of the presently preferred embodiment together with the accompanying drawings in which:

FIG. 1 is a plan view showing an entire configuration of an immune analyzing device equipped with a pipette chip supply device according to one embodiment of the present invention;

FIG. 2 is a front view of a pipette chip supplied by the pipette chip supply device according to one embodiment of the present invention;

FIG. 3 is a perspective view showing an emergency specimen conveying section of the immune analyzing device shown in FIG. 1;

FIG. 4 is a perspective view showing the emergency specimen conveying section of the immune analyzing device shown in FIG. 1;

FIG. 5 is a perspective view showing an entire configuration of the pipette chip supply device according to one embodiment of the present invention;

FIG. 6 is a perspective view showing an entire configuration of a pipette chip supply device according to one embodiment shown in FIG. 5;

FIG. 7 is a side view showing a turning mechanism section of the pipette chip supply device according to one embodiment shown in FIG. 5;

FIG. 8 is a perspective view of when the pipette chip supply device according to one embodiment shown in FIG. 5 is seen from the chip supply mechanism section side;

FIG. 9 is a front view of when the pipette chip supply device according to one embodiment shown in FIG. 5 is seen from the chip supply mechanism section side;

FIG. 10 is a front view of the pipette chip supply device according to one embodiment shown in FIG. 5;

FIG. 11 is a perspective view showing a neutralizing fan of the pipette chip supply device according to one embodiment shown in FIG. 5;

FIG. 12 is a front view showing a state in which a discharge mechanism section of the pipette supply device according to one embodiment shown in FIG. 5 is positioned at a second position;

FIG. 13 is a plan view of a discharge mechanism section of the pipette chip supply device according to one embodiment shown in FIG. 5;

FIG. 14 is a perspective view of the discharge mechanism section of the pipette chip supply device according to one embodiment shown in FIG. 5;

FIG. 15 is a plan view of a movement section of the pipette chip supply device according to one embodiment shown in FIG. 5;

FIG. 16 is a side view of the movement section of the pipette chip supply device according to one embodiment shown in FIG. 5;

FIG. 17 is a front view of a cuvette used in the immune analyzing device shown in FIG. 1;

FIG. 18 is a side view of an emergency specimen conveying section and the specimen dispensing arm of the immune analyzing device shown in FIG. 1;

FIG. 19 is a side view describing the release operation of the pipette chip attached to the specimen dispensing arm of the immune analyzing device shown in FIG. 1;

FIG. 20 is a side view describing the release operation of the pipette chip attached to the specimen dispensing arm of the immune analyzing device shown in FIG. 1;

FIG. 21 is a side view describing the release operation of the pipette chip attached to the specimen dispensing arm of the immune analyzing device shown in FIG. 1;

FIG. 22 is a front view showing a pipette chip supply device according to a first variant of one embodiment shown in FIG. 5;

FIG. 23 is a front view showing a pipette chip supply device according to a second variant of one embodiment shown in FIG. 5;

FIG. 24 is a plan view showing the movement section of the pipette chip supply device according to the second variant shown in FIG. 23;

FIG. 25 is a side view showing the movement section of the pipette chip supply device according to the second variant shown in FIG. 23;

FIG. 26 is a perspective view showing a pipette chip supply device according to a third variant of one embodiment shown in FIG. 5;

FIG. 27 is a front view of the pipette chip supply device according to a third variant shown in FIG. 26 seen from the chip supply mechanism section side;

FIG. 28 is a perspective view showing a pipette chip supply device according to a fourth variant of one embodiment shown in FIG. 5; and FIG. 29 is a block diagram of a control section of the immune analyzing device shown in FIG. 1.

DETAILED DESCRIPTION OF THE PREFERRED EMBODIMENTS

The embodiments of the present invention will now be described based on the drawings.

First, the configuration of an immune analyzing device equipped with a pipette chip supply device according to one embodiment of the present invention will now be described with reference to FIGS. 1 to 18 and FIG. 29.

The immune analyzing device 1 equipped with a pipette chip supply device 30 according to one embodiment of the present invention is a device for performing examination on various items such as hepatitis B, hepatitis C, tumor marker, thyroid hormone and the like using specimens such as blood. The immune analyzing device 1 is configured by a control section 401, a specimen conveying section (sampler) 10, an emergency specimen and chip conveying section 20, a pipette chip supply device 30, a specimen dispensing arm 50, reagent installing sections 61 and 62, a cuvette supply section 70, a primary reaction section 81 and a secondary reaction section 82, reagent dispensing arms 91, 92, 93 and 94, a BF separating section 101 and a BF separating section 102, a conveyance catcher 110, a detecting section 120, a disposing section 130, and a chip releasing section 140, as shown in FIG. 1. In the immune analyzing device 1 according to the present embodiment, the disposable pipette chip 2 (see FIG. 2) is replaced each time suction and discharge of the specimen are performed to suppress the specimen such as blood suctioned and discharged by the specimen dispensing arm 50 from mixing with other specimen.

In the immune analyzing device 1, after the specimen such as blood containing antigen, which is the measurement target, trapped antibody (R1 reagent), magnetic particles (R2 reagent) are mixed, and the antigen, trapped antibody and magnetic particles are bound, the magnetic particles are attracted to a magnet 101d of the BF (Bound Free) separating section 101 thereby removing the solution containing non-reacting (Free) trapped antibody. After binding a labeled antibody (R3 reagent) to the magnetic particles bound with antigen, the bound magnetic particles, antigen, and labeled antibody are attracted to the magnet 102d of the BF separating section 102 thereby removing the R3 reagent containing the non-reacting (free) labeled antibody. Furthermore, after adding a light emitting substrate (R5 reagent) that emits light in the reaction process with the labeled antibody, the light emission amount produced by the reaction between the labeled antibody and the light emitting substrate is measured. The antigen contained in the specimen that binds with the labeled antibody is quantitatively measured through such process.

The control section 401 is mainly configured by a CPU 401b, a ROM 401a, a RAM 401c, and a communication interface 401d, as shown in FIG. 29.

The CPU 401b executes a computer program stored in the ROM 401a, and a computer program read by the RAM 401c. The ROM 401a stores computer programs to be executed by the CPU 401a, data used in the execution of the relevant computer program and the like. The RAM 40ac is used in reading the computer program stored in the ROM 401a. The RAM 401c is also used as a work region of the CPU 401c when executing the computer program.

The communication interface 401d has a function of transmitting a control signal from the CPU 401b for controlling each section such as the mechanism section, detecting section and the sensor of the immune analyzing device 1. The communication interface 401d also has a function of receiving a signal from each section such as the mechanism section, detecting section and the sensor of the immune analyzing device 1.

The specimen conveying section 10 is configured so as to convey a rack 4 mounted with a plurality of test tubes 3 accommodating the specimen to a position corresponding to the suction position 1a of the specimen dispensing arm 50. The specimen conveying section 10 includes a rack set part 10a for setting the rack 4 mounted with the test tube 3 accommodating non-processed specimens, and a rack storage part 10b for storing the rack 4 mounted with the test tube 3 accommodating the dispense processed specimens. When the test tube 3 accommodating the non-processed specimen is conveyed to the position corresponding to the suction position 1a of the specimen dispensing arm 50, the specimen such as blood in the test tube 3 is suctioned by the specimen dispensing arm 50 and the rack 4 mounted with the relevant test tube 3 is stored in the rack storage part 10b.

The emergency specimen and chip conveying section 20 is configured so as to convey the test tube 3 accommodating emergency specimens, which must cut into the specimens being conveyed by the specimen conveying section 10 and examined, to an attachment position 1b of the specimen dispensing arm 50. As shown in FIGS. 1, 3, and 4, the emergency specimen and chip conveying section 20 includes a slide rail 21 arranged so as to extend in the X direction, a linear moving guide including a slide main body 22 arranged movable along the slide rail 21, a conveying rack 23 attached to the slide main body 22, a detection strip 24 attached to the lower part of the conveying rack 23, and a light shielding sensor 25 light shielded by the detection strip 24. Furthermore, the conveying rack 23 is arranged with a test tube installing part 23a for installing the test tube 3 accommodating the emergency specimens, and a chip installing part 23b (see FIG. 4) of a long hole for mounting the pipette chip 2 (see FIG. 2) supplied from the pipette chip supply device 30 to be hereinafter described. The detection strip 24 is arranged so as to light shield the light shielding sensor 25 when arranged at a position of receiving the pipette chip 2 from the pipette chip supply device 30. The conveying rack 23 conveys the test tubes 3 accommodating the emergency specimens and the pipette chip 2 to the attachment position 1b (see FIG. 1) of the specimen dispensing arm 50 by being moved along the slide rail 21 by the driving force from the motor (not shown).

In the present embodiment, the pipette chip supply device 30 has a function of installing one at a time the pipette chip (see FIG. 2) input to a chip refill section 31 to be hereinafter described to the chip installing part 23b of the conveying rack 23 of the emergency specimen and chip conveying section 20. Furthermore, the pipette chip supply device 30 also has a function of supplying the pipette chip to the chip installing part 23b of the conveying rack 23 with the distal end 2a of the pipette chip 2 facing downward. The pipette chip supply device 30 is configured by the chip refill section 31, a turning mechanism section 32, a chip supply mechanism section 33, a conveying path 34, a neutralizing fan 35, a discharge mechanism section 36, a sort mechanism section 37, a movement section 38 and a movement section 39, three shoots 40a to 40c, seven detection sensors (transmissive sensor) 41a to 41h, and a chip collecting container 42, as shown in FIGS. 5 and 6.

The chip refill section 31 is configured so as to be able to accommodate a plurality of refill pipette chips 2 (see FIG. 2). The pipette chips 2 accommodated in the chip refill section 31 is commercially available in bags containing the pipette chips in pluralities (e.g., 500). The pipette chips 2 in bags tend to be charged with static electricity of about a few kV (e.g., about 6 kV) as the pipette chips 2 rub against each other in the transport process of marketing. The chip refill section 31 includes an input port 31a for inputting the plurality of pipette chips 2 taken out from the bag, and a discharge port 31b for discharging the accommodated pipette chips 2, as shown in FIG. 5.

A detection sensor (transmissive sensor) 41a for detecting the presence of the pipette chip 2 accommodated in the chip refill section 31 is arranged at a position in the vicinity of the discharge port 31b of the chip refill section 31.

A shoot 40a for leading the pipette chips 2 dropped from the discharge port 31b to a drum 335 of the chip supply mechanism section 33 to be hereinafter described through an opening 30b (see FIG. 8) of a chassis 30a is arranged at a position of receiving the pipette chip 2 dropped from the discharge port 31b of the chip refill section 31.

The turning mechanism section 32 is configured so as to turn the turning member 323 from a position of blocking the discharge port 31b of the chip refill section 31 to a position of opening the discharge port 31b. The turning mechanism section 32 is configured by a motor 321 acting as a driving source, a pressing member 322 attached to the motor 321, a turning member 323 pressed against the pressing member 322, an extension coil spring 324, and a light shielding sensor 325 (see FIGS. 5 and 6), as shown in FIGS. 6 and 7. The motor 321 is attached to a steel plate 326 attached to the chip refill section 31. One end of the extension coil spring 324 is attached to the steel plate 326, and the other end of the extension coil spring 324 is attached to the turning member 323. In other words, the extension coil spring 324 is arranged so as to bias the turning member 323 in a direction of moving away from the position of blocking the discharge port 31b. A roller 327 for pressing the turning member 323 is attached to the pressing member 322. The light shielding sensor 325 is arranged so as to detect the side surface 323a (see FIG. 5) of the turning member 323 when the turning member 323 is turned to the position of blocking the discharge port 31b.

As shown in FIGS. 8 and 9, the chip supply mechanism section 33 has a function of receiving the pipette chip 2 input through the shoot 40a and the opening 30b of the chassis 30a from the discharge port 31b of the chip refill section 31 and sending some of the received pipette chips 2 to the conveying path 34 to be hereinafter described. The chip supply mechanism section 33 is configured by a stepping motor 331 acting as a driving source, a gear 332 attached to the stepping motor 331, a drum part 333 rotatably attached to the chassis 30a, and a light shielding sensor 334 for detecting the rotating position of the drum part 333. The drum part 333 includes a drum 335 made up of a tubular body capable of accommodating the plurality of pipette chips 2, a chain 336 winded to the periphery of the drum 335 so as to gear with the gear 332, two detection strips 337 detected by the light shielding sensor 334, and a lid 338 (see FIG. 8) attached on the opposite side of the chassis 30a side so as to block the accommodating part 335a of the drum 335 of the tubular body. Two segmenting parts 335b capable of lifting the pipette chips 2 when the drum part 33 rotates are arranged at an interval of 180 degrees on the inner side of the drum 335. The segmenting part 335b has the size and the shape of having the number of pipette chips 2 to be sent to the conveying path 34 to be of a predetermined number (5 to 15 in the present embodiment), and is arranged so as not to send the pipette chips 2 to the conveying path 34 in excess amount. Therefore, the ionized air blown from the neutralizing fan 35 evenly hits the pipette chips 2, thereby effectively performing neutralization. Thus, when the gear 332 rotates by the drive of the stepping motor 331, the chain 336 geared to the gear 332 and the drum 335 winded with the chain 336 rotate. The segmenting part 335b arranged on the inner side of the drum 335 also rotates with the rotation of the drum 335, and the pipette chips 2 accumulated at the lower part in the accommodating part 335a of the drum 335 are lifted by the segmenting part 335b and sent to the conveying path 34 to be hereinafter described through the opening 30c (see FIG. 6) of the chassis 30a. Static electricity is produced at the pipette chips 2 when the pipette chips 2 accommodated inside the drum rub against each other as the drum 335 rotates.

As shown in FIGS. 6 and 10, the conveying path 34 is configured by two inclined paths 34a and 34b for conveying a predetermined amount (about 5 to 15 in the present embodiment) of pipette chips 2 sent from the chip supply mechanism section 33. The inclined paths 34a and 34b of the conveying path 34 are arranged to lead the pipette chips 2 to a partition mechanism section 37 side to be hereinafter described by rolling down the pipette chips 2 sent from the segmenting parts 335b of the drum 335 of the chip supply mechanism section 33. In this case, the ionized air blown from the neutralizing fan 35 hits the pipette chips 2 rolling down the inclined path 34a in a scattering manner, and thus the ionized air evenly hits the pipette chips 2 thereby effectively performing neutralization.

In the present embodiment, the neutralizing fan 35 has a function of blowing ionized air, so that the static electricity charged at the pipette chips 2 can be removed. The neutralizing fan 35 is held so that both side surfaces are sandwiched at a holding part 30d having a horseshoe shape when seen in plan view arranged above the chassis 30a, as shown in FIGS. 5, 8, 10 and 11. The neutralizing fan 35 held at the holding part 30d of the chassis 30a is arranged so that the air blow port 35a faces the opening 30c of the chassis 30a and the portion (region F of FIG. 11) for receiving the pipette chip 2 of the inclined path 34a of the conveying path 34, as shown in FIGS. 8 and 11. In other words, the neutralizing fan 35 is arranged so as to blow the ionized air to the pipette chip 2 lifted by the segmenting part 335b of the drum 355 through the opening 30c of the chassis 30a, and to blow the ionized air to the pipette chip 2 sent from the segmenting part 335b and positioned at the inclined path 34a of the conveying path 34. Furthermore, the neutralizing fan 35 is controlled so as to be driven based on the rotating operation of the drum 35. That is, the neutralizing fan 35 is configured so as to be driven (turned ON) only while the pipette chips 2 are positioned in region F of FIG. 11 by being controlled so as to be driven (turned ON) only for a predetermined time from when the segmenting part 335b of the drum 335 is exposed through the opening 30c of the chassis 30a.

As shown in FIGS. 10 and 12, the discharge mechanism section 36 is configured so as to turn from a first position shown in FIG. 10 at where the pipette chips 2 can be conveyed to a second position (open position) shown in FIG. 12 at where the pipette chips 2 can be discharged. As shown in FIGS. 10, and 12 to 14, the discharge mechanism section 36 is configured by a motor 361 acting as a driving source, a pressing member 362 attached to the motor 361, a turning member 363 pressed against the pressing member 362, an extension coil spring 364, and a light shielding sensor 365. The motor 361 is attached to a steel plate 366 attached to the chassis 30a. One end of the extension coil spring 364 is attached to the steel plate 366, and the other end of the extension coil spring 364 is attached to the turning member 363. In other words, the extension coil spring 364 is arranged so as to bias the turning member 363 in a direction of moving away from the second position (see FIG. 12). A roller 367 for pressing the turning member 363 is attached to the pressing member 362. The turning member 363 includes a slanted surface part 368 configuring the inclined path 34b. The slanted surface part 368 has a function of rolling down the pipette chips 2 received from the inclined path 34a to the partition mechanism section 37 to be hereinafter described through a relay member 40 when turned to the first position, and discharging the pipette chips 2 stuck at the slanted surface part 368 when turned to the second position (open position). The light shielding sensor 365 is arranged so as to detect the detection strip 363a of the turning member 363 when the turning member 363 is turned to the first position.

A detection sensor (transmissive sensor) 41b for detecting the presence of the pipette chip 2 in the slanted surface part 368 is arranged at the position in the vicinity of the slanted surface part 368 of the discharge mechanism section 36. That is, the detection sensor 41b can detect whether or not the pipette chip 2 is stuck at the slanted surface part 368 of the turning member 363.

The sort mechanism section 37 is arranged to sort the pipette chips 2 received from the inclined path 34b by way of the relay member 40 one by one, and to send the pipette chips 2 sorted one by one to the movement section 38 to be hereinafter described. The sort mechanism section 37 includes a cut-out mechanism part 371 for lifting the pipette chips 2 received from the inclined path 34b by way of the relay member 40, a slanted surface part 372 for receiving the pipette chips 2 lifted by the cut-out mechanism part 371 and leading the same to the cut-out mechanism part 373 to be hereinafter described, the cut-out mechanism part 373 for lifting two or less pipette chips 2 received from the slanted surface part 372, and a slanted surface part 374 for receiving the pipette chips 2 lifted by the cut-out mechanism part 373 and sending the same to the movement section 38 to be hereinafter described, as shown in FIGS. 6 and 10.

The cut-out mechanism part 371 is configured by a motor 371a acting as a driving source, a pulley 371b connected to the motor 371a, a pulley 371c arranged at a predetermined distance from the pulley 371b, a drive transmission belt 371d attached to the pulley 371b and the pulley 371c, and a movement member 371e coupled to the drive transmission belt 371d and movable in the up and down direction (Z direction). Thus, when the motor 371a is driven, the drive transmission belt 371d is driven by way of the pulley 371b, whereby the movement member 371e coupled to the drive transmission belt 371d moves in the up and down direction (Z direction).

Therefore, the pipette chips 2 mounted on the upper surface of the movement member 371e are lifted upward and sent to the slanted surface part 372.

The slanted surface part 372 is an inclined surface on which the pipette chips 2 are rolled down from the cut-out mechanism part 371 side towards the cut-out mechanism part 373 side.

Furthermore, the cut-out mechanism part 373 has a function of sending the pipette chips 2 received from the slanted surface part 372 one by one to the slanted surface part 374. As shown in FIG. 10, the cut-out mechanism part 373 is configured by a motor 373a acting as a driving source, a pulley 373b connected to the motor 373a, a pulley 373c arranged at a predetermined distance from the pulley 373b, a drive transmission belt 373d attached to the pulley 373b and the pulley 373c, and a movement member 373e (see FIG. 6) coupled to the drive transmission belt 373d and movable in the up and down direction (Z direction). Thus, when the motor 373a is driven, the drive transmission belt 373d is driven by way of the pulley 373b, whereby the movement member 373e coupled to the drive transmission belt 373d moves in the up and down direction (Z direction). Therefore, the pipette chips 2 mounted on the upper surface of the movement member 373e are lifted upward. The movement member 373e is formed so that only two or less pipette chips 2 are mounted on the upper surface. The movement member 373e is designed so that one of the two pipette chips 2 becomes unbalanced and drops to the slanted surface part 372 side from the upper surface o the movement member 373e even when moved upward (Z direction) with two pipette chips 2 mounted on the upper surface of the movement member 373e. Thus, even if two pipette chips 2 are mounted on the upper surface of the movement member 373e, the pipette chips 2 can be supplied to the slanted surface part 374 one at a time.

The slanted surface part 374 is an inclined surface on which the pipette chips 2 are rolled down from the cut-out mechanism part 373 side towards the movement section 38 side to be hereinafter described, and has a function of supplying the pipette chips 2 to the movement section 38 to be hereinafter described.

The detection sensor (transmissive sensor) 41c is arranged to detect the presence of pipette chips 2 mounted on the upper surface of the movement member 371e of the cut-out mechanism part 371 of the sort mechanism section 37 when the movement member 371e of the cut-out mechanism part 371 of the sort mechanism section 37 is positioned on the lower side. The detection sensor (transmissive sensor) 41c is arranged at a position of a predetermined distance from the detection sensor (transmissive sensor) 41b.

The detection sensor (transmissive sensor) 41d is arranged to detect the presence of the pipette chips 2 mounted on the slanted surface part 372, and control is made such that the cut-out mechanism part 371 of the sort mechanism section 37 does not operate when the detection sensor (transmissive sensor) 41d detects the pipette chip 2.

The movement section 38 is arranged to move the pipette chip 2 rolled down from the slanted surface part 374 of the sort mechanism section 37 in the direction of the arrow X1 (see FIG. 15). As shown in FIG. 15, the movement section 38 is configured by a motor 381 acting as a driving source, a gear 382 attached to the motor 381, a feed screw 383, a shaft 384, a gear 385 attached to the feed screw 383 and geared with the gear 382, and a gear 386 attached to the shaft 384 and geared with the gear 385. The feed screw 383 and the shaft 384 are rotatably attached with respect to the chassis 30a. The feed screw 383 and the shaft 384 are arranged parallel to each other at a distance substantially the same as the diameter of the core 2b (see FIG. 2) of the pipette chip 2. Thus, the feed screw 383 and the shaft 384 are able to hold the core 2b of the pipette chip 2. In this case, the core 2b of the pipette chip 2 held by the feed screw 383 and the shaft 384 is positioned on the upper side from the center of gravity (see FIG. 2) of the pipette chip 2, as shown in FIG. 16, and thus is held by the feed screw 383 and the shaft 384 with the distal end 2a of the pipette chip 2 rolled down from the slanted surface part 374 of the sort mechanism section 37 facing downward. An input part 38a having a spacing greater than the diameter of the attachment part 2c of the pipette chip 2 when seen in plan view is arranged on the side of the direction of the arrow X1 of the feed screw 383 and the shaft 384.

The detection sensor (transmissive sensor) 41e is arranged to detect the presence of the pipette chip 2 held at the feed screw 383 and the shaft 384. The detection sensor (transmissive sensor) 41f is arranged to detect whether or not the pipette chip 2 conveyed by the feed screw 383 and the shaft 384 has been sent to the input part 38a.

The shoot 40b is arranged to lead the pipette chip 2 (see FIG. 2) dropped from the input part 38a (see FIG. 15) of the movement section 38 to the movement section 39.

The movement section 39 is arranged to move the pipette chip 2 led from the movement section 38 by way of the shoot 40b in the direction of the arrow Y1. The movement section 39 is configured by a motor 391 acting as the driving source, a pulley 392 connected to the motor 391, a pulley 393 arranged at a predetermined distance from the pulley 392, a drive transmission belt 394 attached to the pulley 392 and the pulley 393, a feed screw 395 mounted so as to be rotatable with the rotation of the pulley 393, a wall part 396 attached to the chassis 30a, a detection strip 397 attached to the pulley 393, and a light shielding sensor 398, as shown in FIGS. 5, 6, and 10. The feed screw 395 includes a groove part 395a having a diameter smaller than the diameter of the attachment part 2c (see FIG. 2) of the pipette chip 2 and greater than the diameter of the core 2b (see FIG. 2) of the pipette chip 2. The wall part 396 is arranged parallel to the feed screw 295 at a predetermined distance so that the pipette chip 2 fitted to the groove 395a of the feed screw 395 does not drop. The feed screw 395 and the wall part 396 are thereby able to hold the core 2b of the pipette chip 2. The light shielding sensor 398 is arranged to detect the detection strip 397 attached to the pulley 393 when the pulley 393 rotating the feed screw 395 is rotated.

The detection sensor (transmissive sensor) 41g is arranged to detect whether or not the pipette chip 2 led from the movement section 38 by way of the shoot 40b has reached to the movement section 39, as shown in FIGS. 5 and 6. The detection sensor (transmissive sensor) 41h is arranged to detect whether or not the pipette chip 2 conveyed by the movement section 39 has been conveyed up to immediately before being dropped to the shoot 40c to be hereinafter described.

The shoot 40c is arranged to lead the pipette chip 2 conveyed by the movement section 39 to the chip installing part 23b of the conveying rack 23 of the emergency specimen and chip conveying section 20. The shoot 40c is formed so that the distal end 2a of the pipette chip 2 passing therethrough slides down in an inclined state.

The chip collecting container 42 is arranged at a position capable of collecting the pipette chips 2 discharged by the discharge mechanism section 36.

The specimen dispensing arm 50 has a function of dispensing the specimen in the test tube 3 conveyed to the suction position 1a (see FIG. 1) by the specimen conveying section 10 or the specimen in the test tube 3 conveyed to the attachment position 1b (see FIG. 1) by the emergency specimen and chip conveying section 20 to the cuvette 8 (see FIG. 17) held at the holding portion 81b of the rotating table part 81a of the primary reaction section 81 to be hereinafter described. The specimen dispensing arm 50 includes a motor 51, a drive transmitting section 52 connected to the motor 51, and an arm part 54 attached to the drive transmitting section 52 by way of a shaft 53, as shown in FIGS. 1 and 18. The drive transmitting section 52 is configured to turn the arm part 54 with the shaft 53 as the center and move the same in the up and down direction (Z direction) by the driving force from the motor 51. A nozzle portion 54a for suctioning and discharging the specimen is arranged at the distal end of the arm part 54. The pipette chip 2 conveyed by the conveying rack 23 of the emergency specimen and chip conveying section 20 is attached to the distal end 54b of the nozzle portion 54a.

A reagent installing section 61 (see FIG. 1) includes an installing part 61a for installing the reagent bin 5 accommodating the R1 reagent containing trapped antibody and the reagent bin 7 accommodating the R3 reagent containing labeled antibody, an upper surface part 61b arranged at the upper part of the installing part 61a so that foreign materials such as dust do not enter the R1 reagent in the reagent bin 5 or the R3 reagent in the reagent bin 7 installed in the installing part 61a, and a lid part 61c attached to the upper surface part 61b in an openable and closable manner. A groove part 61d to be inserted with a nozzle 91e of the reagent dispensing arm 91 to be hereinafter described, and a groove part 61e to be inserted with a nozzle 93e of the reagent dispensing arm 93 are formed in the upper surface part 61b. The installing part 61a is rotatably configured so as to convey the installed reagent bin 5 and the reagent bin 7 to the position corresponding to the groove part 61d and the groove part 61e of the upper surface part 61b.

The reagent installing section 62 (see FIG. 1) includes an installing part 62a for installing a reagent bin 6 accommodating the R2 reagent containing magnetic particles, an upper surface part 62b arranged at the upper part of the installing part 62a-so that foreign materials such as dust do not enter the R2 reagent in the reagent bin 6 installed in the installing part 62a, and a lid part 62c attached to the upper surface part 62b in an openable and closable manner. A groove part 62d to be inserted with a nozzle 92e of the reagent dispensing arm 92 to be hereinafter described is formed in the upper surface part 62b. The installing part 62a is rotatably configured so as to convey the installed reagent bin 6 to a position corresponding to the groove part 62d.

A cuvette supply section 70 (see FIG. 1) is configured so as to be able to sequentially supply a plurality of cuvettes 8 (see FIG. 17) to a holding portion 81b of the rotating table part 81a of the primary reaction section 81. The cuvette supply section 70 includes a hopper 71 capable of accommodating the plurality of cuvettes 8, two guiding plates 72 arranged below the hopper 71, a supporting table 73 arranged at the lower end of the guiding plate 72, and a supply catcher part 74. The two guiding plates 72 are arranged parallel to each other at a distance smaller than the diameter of a collar part 8a (see FIG. 17) of the cuvette 8 and larger than the diameter of a core 8b (see FIG. 17) of the cuvette 8. The plurality of cuvettes 8 supplied to the hopper 71 are arrayed along the guiding plate 72 with the collar part 8a engaging the upper surface of the two guiding plates 72 by applying vibration to the hopper 71. The supporting table 73 includes a rotating part 73a arranged rotatable with respect to the supporting table 73, and a concave part 73b arranged so as to be adjacent to the rotating part 73a. Three cut-outs 73c are formed on the outer peripheral portion of the rotating part 73a at every predetermined angle (120° in the present embodiment). The cut-out 73c is arranged to accommodate the cuvette 8 guided by the guiding plate 72 one by one. The concave part 73b is configured so as to receive the cuvette 8 that rotates in a state accommodated in the cut-out 73c of the rotating part 73a.

The supply catcher part 74 (see FIG. 1) has a function of moving the cuvette 8 received by the concave part 73b to the holding portion 81b of the rotating table part 81a of the primary reaction section 81. The supply catcher part 74 includes a motor 74a, a pulley 74b connected to the motor 74a, a pulley 74c arranged at a predetermined distance from the pulley 74b, a drive transmission belt 74d attached to the pulley 74b and the pulley 74c, an arm part 74e attached to the pulley 74c by way of a shaft, and a driving part 74f for moving the arm part 74e in the up and down direction (Z direction). A chuck part 74g for sandwiching and gripping the cuvette 8 is arranged at the distal end of the arm part 74e.

The primary reaction section 81 (see FIG. 1) is arranged to rotatably move the cuvette 8 held by the holding portion 81b of the rotating table part 81a over a predetermined angle at every predetermined period (18 seconds in the present embodiment), and to stir the specimen, R1 reagent and the R2 reagent in the cuvette 8. The primary reaction section 81 is configured by a rotating table part 81a for conveying the cuvette 8 accommodating the specimen, the R1 reagent, and the R2 reagent in the rotating direction, and a conveying mechanism part 81c for stirring the specimen, the R1 reagent and the R2 reagent in the cuvette 8 and conveying the cuvette 8 accommodating the stirred specimen, the R1 reagent and the R2 reagent to the BF separating section 101 to be hereinafter described.

The reagent dispensing arm 91 (see FIG. 1) has a function of suctioning the R1 reagent in the reagent bin 5 installed in the installing part 61a of the reagent installing section 61 and dispensing the suctioned R1 reagent to the cuvette 8 dispensed with the specimen of the holding portion 81b of the rotating table part 81a of the primary reaction section 81. The reagent dispensing arm 91 includes a motor 91a, a drive transmission part 91b connected to the motor 91a, and an arm part 91d attached to the drive transmission part 91b by way of a shaft 91c. The drive transmission part 91b is configured to turn the arm part 91d with the shaft 91c as the center and move the same in the up and down direction (Z direction) by the driving force from the motor 91a. The nozzle 91e for suctioning and discharging the R1 reagent in the reagent bin 5 is attached to the distal end of the arm part 91d. That is, the nozzle 91 suctions the R1 reagent in the reagent bin 5 through the groove part 61d of the upper surface part 91e of the reagent installing section 61, and thereafter the suctioned R1 reagent is dispensed into the cuvette 8 dispensed with the specimen.

The reagent dispensing arm 92 (see FIG. 1) has a function of dispensing the R2 reagent in the reagent bin 6 installed in the installing part 62a of the reagent installing section 62 into the cuvette 8 dispensed with the specimen and the R1 reagent of the primary reaction section 81. The reagent dispensing arm 92 includes a motor 92a, a drive transmission part 92b connected to the motor 92a, and an arm part 92d attached to the drive transmission part 92b by way of a shaft 92c. The drive transmission part 92b is configured so as to turn the arm part 92d with the shaft 92c as the center and move the same in the up and down direction (Z direction) by the driving force from the motor 92a. A nozzle 92e for suctioning and discharging the R2 reagent in the reagent bin 6 is attached to the distal end of the arm part 92d. Therefore, the nozzle 92e suctions the R2 reagent in the reagent bin 6 by way of the groove part 62d of the upper surface part 62b of the reagent installing section 62, and thereafter the suctioned R2 reagent is dispensed into the cuvette 8 dispensed with the specimen and the R1 reagent.

The BF (Bound Free) separating section 101 (see FIG. 1) is arranged to remove the non-reacting R1 reagent in the cuvette 8 (see FIG. 17) received from the conveying mechanism part 81c of the primary reaction section 81. The BF separating section 101 includes an installing part 101a for installing the cuvette 8 and conveying the same in the rotating direction, and a separation stirring part 101b for suctioning the non-reacting R1 reagent. The installing part 101a includes three installation holes 101c for holding the cuvette 8, and a magnet 101d arranged lateral to each of the three installation holes 101a. Thus, the bound antigen, trapped antibody and magnetic particles in the cuvette 8 installed in the installation hole 101c can be attracted to the magnet 101d side. Furthermore, the non-reacting (free) R1 reagent not binding with the magnetic particles can be removed by suctioning the specimen and the like in the cuvette 8 in the attracted state by means of the separation stirring part 101b.

A conveyor catcher section 110 (see FIG. 1) has a function of conveying the cuvette 8 (see FIG. 17) of the installing part 101a of the BF separating section 101 in which the non-reacting R1 reagent etc. is separated to the holding portion 82b of the rotating table part 82a of the secondary reaction section 82. The conveying catcher section 110 includes a motor 110a, a pulley 10b connected to the motor 11a, a pulley 110c arranged at a predetermined distance from the pulley 110b, a drive transmission belt 110d attached to the pulley 110b and the pulley 110c, an arm part 110e attached to the pulley 110c by way of a shaft, and a driving part 10f for moving the arm part 110e in the up and down direction (Z direction). A chuck part 110g for sandwiching and gripping the cuvette 8 is arranged at the distal end of the arm part 110e.

The secondary reaction section 82 (see FIG. 1) has a configuration similar to the primary reaction section 81, and is arranged to rotatably move the cuvette 8 held at the holding portion 82b of the rotating table part 82a over a predetermined angle at every predetermined period (18 seconds in the present embodiment), and stir the specimen, R1 reagent, R2 reagent, R3 reagent and R5 reagent in the cuvette 8. The secondary reaction section 82 is configured by a rotating table part 82a for conveying the cuvette 8 accommodating the specimen, R1 reagent, R2 reagent, R3 reagent and R5 reagent in the rotating direction, and a conveying mechanism part 82c for stirring the specimen, R1 reagent, R2 reagent, R3 reagent, and R5 reagent in the cuvette 8 and conveying the cuvette 8 accommodating the stirred specimen and the like to the conveying to the BF separating section 102 to be hereinafter described. Furthermore, the conveying mechanism part 82c has a function of conveying the cuvette 8 processed by the BF separating section 102 again to the holding portion 82b of the rotating table part 82a.

The reagent dispensing arm 93 (see FIG. 1) has a function of suctioning the R3 reagent in the reagent bin 7 installed in the installing part 61a of the reagent installing section 61 and dispensing the suctioned R3 reagent into the cuvette 8 dispensed with the specimen, R1 reagent, and R2 reagent of the secondary reaction section 82. The reagent dispensing arm 93 includes a motor 93a, a drive transmission part 93b connected to the motor 93a, and an arm part 93d attached to the drive transmission part 93b by way of a shaft 93c. The drive transmission part 93b is configured so as to turn the arm part 93d with the shaft 93c as the center and move the same in the up and down direction (Z direction) by the driving force from the motor 93a. A nozzle 93e for suctioning and discharging the R3 reagent in the reagent bin 7 is attached to the distal end of the arm part 93d. That is, the nozzle 93e suctions the R3 reagent in the reagent bin 7 through the groove part 61e of the upper surface part 61b of the reagent installing section 61, and thereafter, the suctioned R3 reagent is dispensed into the cuvette 8 dispensed with the specimen, R1 reagent, and R2 reagent.

The BF separating section 102 (see FIG. 1) has a configuration similar to the BF separating section 101, and is arranged to remove the non-reacting R3 reagent in the cuvette 8 (see FIG. 17) received from the conveying mechanism part 82c of the secondary reaction section 82. The BF separating section 102 includes an installing part 102a for installing the cuvette 8 and for conveying the same in the rotating direction, and a separation stirring part 102b for suctioning the non-reacting R3 reagent. The installing part 102a includes three installation holes 102c for holding the cuvette 8, and a magnet 102d arranged lateral to each of the three installation holes 101a. Thus, the bound magnetic particles, antigen, and labeled antibody in the cuvette 8 installed in the installation hole 102c can be attracted to the magnet 102d side. Furthermore, the non-reacting (free) R3 reagent can be removed by suctioning the specimen and the like in the cuvette 8 in the above attracted state by means of the separation stirring part 102b.

The reagent dispensing arm 94 (see FIG. 1) has a function of dispensing the R5 reagent containing light emitting substrates in a reagent bin (not shown) installed at the lower part of the immune analyzing device 1 into the cuvette 8 accommodating the specimen, R1 reagent, and R2 reagent, and R3 reagent of the secondary reaction section 82. The reagent dispensing arm 94 includes a motor 94a, a drive transmission part 94b connected to the motor 94a, and an arm part 94d attached to the drive transmission part 94b by way of a shaft. The drive transmission part 94b is configured so as to turn the arm part 94d with the shaft as the center and move the same in the up and down direction (Z direction) by the driving force from the motor 94a. A nozzle (not shown) for suctioning and discharging the R5 reagent is attached to the distal end of the arm part 94c.

The detecting section 120 (see FIG. 1) is arranged to acquire the light produced in the reaction process of the labeled antibody that binds with the antigen of the specimen performed with a predetermined process and the light emitting substrate by means of a photo multiplier tube to measure the amount of antigen contained in the relevant specimen. The detecting section 120 is configured by an installing part 121 for installing the cuvette 8 accommodating the specimen, R1 reagent, R2 reagent, R3 reagent, and R5 reagent, and a conveying mechanism part 122 for conveying the cuvette 8 (see FIG. 17) held at the holding portion 82b of the rotating table part 82a of the secondary reaction section 82.

The disposing section 130 (see FIG. 1) is arranged to dispose the measured specimen etc. measured by the detecting section 120, and the cuvette 8 (see FIG. 17) accommodating the relevant specimen etc. The disposing section 130 is configured by a suction part 131 for suctioning the specimen and various regents in the cuvette 8, and a disposing hole 132 arranged at a position at a predetermined distance from the suction part 131. Thus, the suction part 131 suctions the measured specimen etc., and thereafter the used cuvette 8 is disposed into a dust box (not shown) arranged at the lower part of the immune analyzing device 1 through the disposing hole 132.

The chip releasing section 140 (see FIG. 1) is arranged to release the pipette chip 2 attached to the specimen dispensing arm 50. The chip releasing section 140 includes a steel plate 141 arranged so as to extend in the vertical direction (Z direction), and a release strip 142 made of resin attached to the steel plate 141, as shown in FIG. 19. A cut-out part 142a having a diameter smaller than the diameter of the attachment part 2c (see FIG. 21) of the pipette chip 2 and greater than the diameter of the distal end 54b (see FIG. 21) of the specimen dispensing arm 50 is formed in the release strip 142.

The supply operation of the pipette chip with respect to the specimen dispensing arm of the pipette chip supply device will now be described with reference to FIGS. 2 to 6, 8, 10, 12, 15, 16, and 18.

As shown in FIG. 5, a plurality of pipette chips 2 are first input from the input port 31a of the chip refill section 31 of the pipette supply device 30. In this case, the turning member 323 of the turning mechanism section 32 is turned to the position of blocking the discharge port 31b of the chip refill section 31, and the plurality of pipette chips 2 are accumulated in the chip refill section 31. The pipette chips 2 in the chip refill section 31 are detected by the detection sensor (transmissive sensor) 41a.

When the turning member 323 of the turning mechanism section 32 is turned to the position of opening the discharge port 31b of the chip refill section 31, a predetermined amount of pipette chips 2 are input to the drum 335 of the chip supply section 33 from the discharge port 31b of the chip refill section 31 through the shoot 40a and the opening 30b (see FIG. 8) of the chassis 30a.

When the detection sensor (transmissive sensor) 41b shown in FIGS. 5 and 10 does not detect the pipette chip 2 on the slanted surface part of the discharge mechanism section 36, the drum part 333 of the chip supply mechanism section 33 is rotated, and a predetermined amount (5 to 15 in the present embodiment) of pipette chips 2 are sent to the conveying path 34 by the segmenting part 335b. The segmenting part 335b has the size and the shape of having the number of pipette chips 2 to be sent to the conveying path 34 at a predetermined amount (5 to 15 in the present embodiment), and thus does not send an excess amount of pipette chips 2 to the conveying path 34. Therefore, the ionized air blown from the neutralizing fan 35 evenly hits the pipette chips 2, and neutralization is effectively performed. When the detection sensor 41b detects the pipette chips 2 on the slanted surface part 368 of the discharge mechanism section 36, the drum part 333 of the chip supply mechanism section 33 is not rotated, and the pipette chips 2 are not supplied to the conveying path 34.

In the present embodiment, the pipette chips 2 sent to the conveying path 34 by the segmenting part 335b of the drum 335 of the chip supply mechanism section 33 rolls down the inclined path 34a of the conveying path 34 while having the static electricity removed by the ionized air blown from the neutralizing fan 35, as shown in FIG. 11. The ionized air blown from the neutralizing fan 35 hits the pipette chips 2 rolling down the inclined path 34a while scattering, and thus the ionized air evenly hits the pipette chips 2, and neutralization is effectively performed. According to the experiments of the inventors, the result that the voltage of the pipette chip 2 charged with static electricity of a voltage of a few kV lowers to a few V is obtained.

As shown in FIG. 6, the pipette chip 2 rolled down from the inclined path 34a of the conveying path 34 rolls down the slanted surface part 368 of the discharge mechanism section 36 configuring the inclined path 34b of the conveying path 34 to be led to the cut-out mechanism part 371 of the sort mechanism section 37 by way of the relay member 40. In this case, the presence of the pipette chip 2 on the slanted surface part 368 of the discharge mechanism section 36 is detected by the detection sensor (transmissive sensor) 41b, and the presence of the pipette chip 2 on the movement member 371e of the cut-out mechanism part 371 is detected by the detection sensor (transmissive sensor) 41c.

When the detection sensors 41b and 41c detect the pipette chip 2 even when the movement member 371e of the cut-out mechanism part 371 is moved in the up and down direction over a predetermined number of times (e.g., 15 times), the pipette chip 2 is determined as being stuck at the slanted surface part 368 of the discharge mechanism section 36, and thus the turning member 363 of the discharge mechanism section 36 is turned and the slanted surface part 368 is separated away from the relay member 40, as shown in FIG. 12. The pipette chip 2 stuck at the slanted surface part 368 is thereby dropped downward, and collected by the chip collecting container 42. The above operation is performed under the condition that the pipette chip 2 on the slanted surface part 372 is not detected by the detection sensor (transmissive sensor) 41b.

Subsequently, the pipette chip 2 mounted on the movement member 371e of the cut-out mechanism part 371 is lifted and sent to the slanted surface part 372 side by moving the movement member 371e of the cut-out mechanism part 371 of the sort mechanism section 37 in the up and down direction (Z direction). In this case, the presence of the pipette chip 2 mounted on the slanted surface part 372 is detected by the detection sensor (transmissive sensor) 41d, where when the pipette chip 2 is detected by the detection sensor 41d, the operation of the cut-out mechanism part 371 is stopped, thereby stopping the pipette chip 2 from being sent from the cut-out mechanism part 371 to the slanted surface part 372.

The pipette chip 2 lifted to the slanted surface part 372 from the cut-out mechanism part 371 of the sort mechanism section 37 is then rolled down the slanted surface part 372 and led to the cut-out mechanism part 373. Thereafter, the pipette chip 2 mounted on the movement member 373e of the cut-out mechanism part 373 is lifted and sent to the slanted surface part 374 by moving the movement member 373e of the cut-out mechanism part 373 in the up and down direction (Z direction). The pipette chip 2 lifted to the slanted surface part 374 rolls down the slanted surface part 374 and sent to the movement section 38.

As shown in FIG. 16, the pipette chip 2 rolled down from the slanted surface part 374 of the sort mechanism section 37 has the core 2b (see FIG. 2) at the position above the center of gravity G held by the feed screw 383 and the shaft 384, and thus the distal end 2a of the pipette chip 2 is directed downward.

The presence of the pipette chip 2 held by the feed screw 383 and the shaft 384 is detected by the detection sensor (transmissive sensor) 41e shown in FIGS. 5 and 15. Specifically, when the detection sensor 41e does not detect the pipette chip 2 held by the feed screw 383 and the shaft 384, one pipette chip 2 is sent from the slanted surface part 374 of the sort mechanism section 37 to the movement section 38 by moving the cut-out mechanism part 371 and the cut-out mechanism part 373 of the sort mechanism section 37 in the up and down direction (Z direction), as shown in FIG. 6. On the other hand, when the detection sensor 41e detects the pipette chip 2 held by the feed screw 383 and the shaft 384, the supply of pipette chip 2 to the movement section 38 is stopped by stopping the movement of the cut-out mechanism part 371 and the cut-out mechanism part 373 of the sort mechanism section 37 in the up and down direction (Z direction).

The pipette chip 2 held by the feed screw 383 and the shaft 384 is conveyed to the input part 38a (see FIG. 15) of the movement section 38 by rotating the feed screw 383 and the shaft 384 of the movement section 38. In this case, whether or not the pipette chip 2 sent by the feed screw 383 and the shaft 384 has been conveyed to the input part 38a is detected by the detection sensor (transmissive sensor) 41f, as shown in FIG. 15.

As shown in FIG. 6, the pipette chip 2 dropped from the input part 38a of the movement section 38 passes through the shoot 40b and reaches the movement section 39. In this case, whether or not the pipette chip 2 has reached the movement section 39 is detected by the detection sensor (transmissive sensor) 41g. Specifically, if the detection sensor 41g detects the pipette chip 2, the operation of the movement section 38 is stopped, thereby stopping the pipette chip 2 from being sent from the movement section 38 to the movement section 39. On the other hand, if the detection sensor 41g does not detect the pipette chip 2, the pipette chip 2 is supplied from the movement section 38 to the movement section 39 by rotating the feed screw 383 and the shaft 384 of the movement section 38.

The pipette chip 2 held one by one at the groove part 395a and the wall part 396 of the feed screw 395 is sequentially conveyed to the shoot 40c by rotating the feed screw 395 of the movement section 39. In this case, the detection sensor (transmissive sensor) 41h detects the presence of the pipette chip 2 at the position immediately before the shoot 40c. Specifically, the pipette chip 2 is rapidly conveyed to the position immediately before the shoot 40c by rotating the feed screw 395 until the detection sensor 41h detects the pipette chip 2 at the position immediately before the shoot 40c.

As shown in FIGS. 3 and 4, the pipette chip 2 sequentially conveyed one at a time by the movement section 39 passes through the shoot 40c and installed at the chip installing part 23b of the conveying rack 23 of the emergency specimen and chip conveying section 20. In this case, the emergency specimen and chip conveying section 20 is recognized as being arranged at a position capable of receiving the pipette chip 2 from the shoot 40c when the detection strip 24 of the emergency specimen and chip conveying section 20 is detected by the light shielding sensor 25, as shown in FIG. 3.

The pipette chip 2 mounted on the chip installing part 23b of the conveying rack 23 is conveyed to a position corresponding to the attachment position 1b (see FIG. 1) of the specimen dispensing arm 50. As shown in FIG. 18, the distal end 54b of the nozzle portion 54a of the arm part 54 is press fit into the attachment part 2c of the pipette chip 2 by moving the arm part 54 downward after turning the nozzle portion 54a of the arm part 54 of the specimen dispensing arm 50 to the attachment position 1b (see FIG. 1). The pipette chip 2 is thereby supplied from the pipette chip supply device 30 to the specimen dispensing arm 50.

FIGS. 19 to 21 are side views for explaining the release operation of the pipette chip attached to the specimen dispensing arm of the immune analyzing device shown in FIG. 1. The release operation of the pipette chip attached to the specimen dispensing arm will now be described with reference to FIGS. 19 to 21.

First, as shown in FIG. 19, the arm part 54 attached with the used pipette chip 2 is moved downward, and the arm part 54 is turned so that the nozzle portion 54a of the arm part 54 fits into the cut-out part 142a of the release strip 142 of the chip release section 140. The arm part 54 is then moved upward from this state to contact the lower surface of the release strip 142 of the chip release section 140 and the upper surface of the attachment part 2c of the pipette chip 2, as shown in FIG. 20. Subsequently, the arm part 54 is moved upward to release the pipette chip 2 from the distal end 54b of the nozzle portion 54a of the arm part 54, as shown in FIG. 21.

In the present embodiment, the neutralizing fan 35 is arranged so as to blow the ionized air against the pipette chip 2 lifted by the segmenting part 335b of the drum 335, and to blow the ionized air against the pipette chip 2 positioned at the inclined path 34a of the conveying path 34 sent from the segmenting part 335b through the opening 30c of the chassis 30a, so that pipette chip 2 is suppressed from attaching to the segmenting part 335b of the chip supply mechanism section 33, conveying path 34, relay member 40, sort mechanism section 37, movement section 38, shoot 40b, movement section 39 and shoot 40c on the supply path or the pipette chips 2 from attaching to each other due to the electrification charge of the pipette chip 2, whereby the pipette chip 2 can be smoothly supplied to the chip installing part 23b of the conveying rack 23 of the emergency specimen and chip movement section 20.

Furthermore, in the present embodiment, the pipette chip 2 can be sorted by ones and supplied with the distal end 2a facing downward by arranging the sort mechanism section 37 for sorting the pipette chips 2 received from the conveying path 34 one by one, and the movement sections 38 and 39 for directing and moving the sorted pipette chip 2 with the distal end 2a facing downward. As a result, the supplied pipette chip 2 can be easily attached to the specimen dispensing arm 50 one at a time in the immune analyzing device 1 equipped with the specimen dispensing arm 50 employing the supplied pipette chip 2.

In the present embodiment, by arranging the detection sensors 41b and 41c for detecting the stuck of the pipette chip 2 at the slanted surface part 368 of the discharge mechanism section 36 and at the movement member 371e of the cut-out mechanism part 371 or the supply path of the pipette chip 2, and the discharge mechanism section 36 for discharging the pipette chip 2 on the inclined path 45b (slanted surface part 368) of the conveying path 34 when the stuck of the pipette chip 2 is detected by the detection sensors 41b, 41b, when the pipette chip 2 is stuck at the slanted surface part 368 of the discharge mechanism section 36 and the movement member 371e of the cut-out mechanism part 371, the stuck of the pipette chip 2 is detected by the detection sensors 41b and 41c, and the stuck pipette chip 2 can be discharged from the inclined path 34b of the conveying path 34 by turning the turning member 363 of the discharge mechanism section 36 to the second position (open position) based on the detected information. As a result, the pipette chips 2 are suppressed from accumulating at the conveying path 34 of the pipette chip 2.

In the present embodiment, by attaching the slanted surface part 368 made of resin having substantially the same inclination as the upper surface of the movement member 371e of the cut-out mechanism part 371 and the upper surface of the relay member 40 configuring the inclined path 34b to the turning member 363 of the discharge mechanism section 36 when the turning member 363 is moved to the first position, the pipette chip 2 that passes through the movement member 371e, the relay member 40 and the slanted surface part 368 of the turning member 363 of substantially the same inclination can be smoothly dropped, and thus the pipette chip 2 is suppressed from being stuck near the boundary of the relay member 40 and the slanted surface part 368, and near the boundary of the movement member 371e and the relay member 40. Furthermore, by forming the slanted surface part 368 from synthetic resin, the slanted surface part 368 having substantially the same inclination as the upper surface of the movement member 371e and the upper surface of the relay member 40 can be easily formed.

In the present embodiment, by arranging the detection sensor 41b for detecting the presence of the pipette chip 2 at the slanted surface part 368 of the turning member 363 and the detection sensor 41c for detecting the presence of the pipette chip 2 in the cut-out mechanism part 371 of the sort mechanism section 37, whether the pipette chip 2 is stuck at the slanted surface part 368 and the cut-out mechanism section 371 can be reliably detected by detecting the presence of the pipette chip 2 with two detection sensors 41b and 41c.

In the present embodiment, the detection sensors 41b and 41c for detecting the presence of the pipette chip 2 are respectively arranged in the slanted surface part 368 of the turning member 363 and the cut-out mechanism part 371 of the sort mechanism section 37 or the supply path of the pipette chip 2, and further, the operation of the drum part 333 of the chip supply mechanism section 33 for sending out the pipette chip 2 is controlled based on the presence of the pipette chip 2 detected by the detection sensors 41b and 41c, so that the pipette chip 2 can be sent out to the conveying path 34 by operating the drum part 333 when there are no pipette chip 2 to be supplied to the sort mechanism section 37. Therefore, a predetermined amount of pipette chip 2 can be refilled to the conveying path 34 to supply to the sort mechanism section 37. Furthermore, when there are pipette chips 2 to be supplied to the sort mechanism section 37 in the conveying path 34, the excess amount of pipette chip 2 is suppressed from being conveyed by stopping the drum part 333. Thus, the pipette chip 2 is suppressed from being stuck that occurs when excess amount of pipette chip 2 is conveyed to the conveying path 34. As a result, the pipette chips 2 are suppressed from accumulating in the conveying path 34 or the supply path of the pipette chip 2.

In the present embodiment, by arranging the detection sensors 41e and 41f for detecting the presence of the pipette chip 2 moved by the movement section 38, and controlling the operation of the sort mechanism section 37 for supplying the pipette chip 2 to the movement section 38 based on the presence of the pipette chip 2 detected by the detection sensors 41e and 41f, the pipette chip 2 can be sent out from the sort mechanism section 37 to the movement section 38 by operating the sort mechanism section 37 when the detection sensors 41e and 41f do not detect the pipette chip 2 to be moved in the movement section 38. Thus, the pipette chip 2 to be moved by the movement section 38 can be refilled. When the pipette chip 2 moved by the movement section 38 is detected by the detection sensors 41e and 41f, the excess amount of pipette chip 2 is suppressed from being sent out to the movement section 38 by stopping the operation of the sort mechanism section 37. Thus, the pipette chip 2 is suppressed from being stuck that occurs when excess amount of pipette chip 2 is conveyed to the movement section 38. As a result, the pipette chip 2 is suppressed from being accumulating at the supply path (movement section 38) of the pipette chip 2.

The embodiments disclosed herein are merely illustrative in all aspects and should not be construed as being exclusive. The scope of the present invention is defined not by the description of the above described embodiment but by the scope of the claims, and thus encompasses all modifications equivalent in meaning to and within the scope of the claims.

In the embodiment, an example of applying the pipette chip supply device for supplying the disposable pipette chip one at a time to the immune analyzing device has been described, but the present invention is not limited thereto, and may be applicable to devices other than the immune analyzing device as long as the device uses disposable pipette chips.

In the embodiment, an example of ON/OFF controlling the drive of the neutralizing fan based on the rotating operation of the drum has been described, but the present invention is not limited thereto, and the neutralizing fan may be driven constantly while the pipette chip supply device is being driven irrespective of the rotating operation of the drum.

In the embodiment, an example of arranging the neutralizing fan 35 so as to blow the ionized air to the pipette chip 2 lifted by the segmenting part 335b of the drum 335 and so as to blow the ionized air to the pipette chip 2 positioned at the inclined path 34a of the conveying path 34 sent from the segmenting part 335b through the opening 30c of the chassis 30a has been described, but the present invention is not limited thereto, and the neutralizing fan 35 may be arranged above the movement section 39 so as to blow the ionized air to the pipette chip 2 moved by the movement section 39 as in the pipette chip supply device 130a of the first variant shown in FIG. 22. In this case, the drive of the neutralizing fan 35 may be controlled based on the drive of the movement section 39, or the neutralizing fan 35 may be driven constantly while the pipette chip supply device 130 is being driven irrespective of the drive of the movement section 39.

In the embodiment, an example of removing electrification charge of the pipette chip 2 by blowing the ionized air from the neutralizing fan 35 has been described, but the present invention is not limited thereto, and the electrification charge of the pipette chip may be removed by contacting the conductive member to the pipette chip. For example, the electrification charge of the pipette chip 2 may be removed by contacting the neutralizing brush 351 to the pipette chip 2 as in the pipette chip supply device 130b of the second variant shown in FIGS. 23 to 25. Specifically, in the pipette chip supply device 130b of the second variant, the neutralizing brush 351 including a brush part 351a made of fiber having electrical conductivity such as carbon fiber, stainless fiber etc., and a holder part 351b for supporting the brush part 351a is attached to the protective cover 399 of the movement section 39, as in FIGS. 24 and 25. The brush part 351a of the neutralizing brush 351 has flexibility. Thus, since the pipette chip 2 moved while being held by the feed screw 395 and the wall part 396 of the movement section 39 contacts the brush part 351a of the neutralizing brush 351, the electrification charge of the pipette chip 2 is removed, and accumulation of the pipette chip 2 that occurs when the pipette chip 2 contacts the brush part 351a of the neutralizing brush 351 is suppressed. The electrification charge of the pipette chip 2 can be removed by contacting the neutralizing sheet 352 to the pipette chip 2 as in the pipette chip supply device 130c of the third variant, shown in FIGS. 26 and 27. Specifically, in the pipette chip supply device 130c according to the third variant, the neutralizing sheet 352 is attached to the inner peripheral surface of the drum 335, the surface of the inclined paths 34a and 34b of the conveying path 34, the surface of the relay member 40, the surfaces of the cut-out mechanism parts 371 and 373 and the slanted surface parts 372 and 374 of the sort mechanism section 37, and the surface of the wall part 396 of the movement section 39, as shown in FIGS. 26 and 27. Thus, the electrification charge of the pipette chip 2 can be removed since the pipette chip 2 contacts the neutralizing sheet 352 on the supply path of the pipette chip 2. The neutralizing sheet 352 has a thickness of about 0.3 mm to about 0.5 mm and is interworked with fiber having electrical conductivity such as carbon fiber, stainless fiber and the like. The neutralizing sheet 352 may be a plate member or foil member having electrical conductivity.

In the embodiment, an example of conveying the pipette chip 2 while holding the same with the feed screw 395 and the wall part 396 in the movement section 39 has been described, but the present invention is not limited thereto, and the pipette chip 2 sorted one by one may be sandwiched and held by two belts, and sequentially conveyed one at a time.

In the embodiment, an example of accommodating a plurality of refill pipette chips in the chip refill section, and thereafter inputting the plurality of pipette chips from the chip refill section to the drum through the shoot has been described, but the present invention is not limited thereto, and the plurality of pipette chips may be directly input to the drum.

In the embodiment, an example in which the segmenting part lifts the pipette chip accumulated at the lower part and sending out the pipette chip to the conveying path by rotating the drum has been described, but the present invention is not limited thereto, and a predetermined amount of pipette chips may be sent out to the conveying path by the conveying belt from locations where the pipette chips are accommodated, or the pipette chips may be lifted and sent out to the conveying path as in the cut-out mechanism part of the sort mechanism section of the present embodiment.

In the embodiment, an example in which the pipette chips 2 stuck at the conveying path 34 is dropped into the chip collecting container 42 by turning the turning member 363 of the discharge mechanism section 36 to the second position has been described, but the present invention is not limited thereto, and the slanted surface part 43 may be arranged at the position where the pipette chip 2 discharged from the discharge mechanism section 36 is dropped, and the opening 30d for returning the pipette chip 2 sled down the slanted surface part 43 to the drum 335 of the drum part 333 may be formed in the chassis 30a so as to return the pipette chip 2 stuck at the conveying path 34 again to the drum 335 of the drum part 333. Thus, the pipette chip 2 stuck at the conveying path 34 can be reused by returning the pipette chip 2 stuck at the conveying path 34 again to the drum 335 of the drum part 333. In this case, as the distal end 2a of the pipette chip 2 enters from the opening on the attachment part 2c side of the other pipette chip 2, even if the plurality of pipette chips 2 are overlapped, such overlap can be eliminated by rotating the overlapped pipette chips 2 at the drum part 333.

In the embodiment, an example of dropping the pipette chip discharged from the discharge mechanism section to the chip collecting container has been described, but the present invention is not limited thereto, and similar to the disposing hole of the disposing section of the immune analyzing device, the pipette chip discharged from the discharge mechanism section may be disposed to a dust box at the lower part of the immune analyzing device.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

What is claimed is:

1. An automated biological sample dispensing apparatus comprising:
    a pipette chip supply device comprising
        a chip accommodating section configured to accommodate pipette chips,
        a conveying section configured to convey the pipette chips supplied from the chip accommodating section one by one to a chip attaching position and
        a static eliminator configured to remove electrification charge of the pipette chips;
    a container transport device configured to transport a container to a dispensing position; and
    a sample dispense device configured to attach the conveyed pipette chip at the chip attaching position and to dispense a biological sample to the transported container at the dispensing position by using the attached pipette chip,
    wherein the conveying section comprises
        a first shaft and
        a rotatable feed screw arranged in parallel to the first shaft at a predetermined distance, the first shaft and the feed screw being configured to hold the supplied pipette chip and to transfer the supplied pipette chip by rotation of the feed screw,
    wherein the sample dispense device comprises
        a second shaft,
        an arm part connected to the second shaft and having a nozzle which is configured to attach a pipette chip, and
        a motor for turning the arm part through the second shaft.

2. The automated biological sample dispensing apparatus according to claim 1, wherein the static eliminator removes the electrification charge of the pipette chips positioned at the chip accommodating section or the conveying section.

3. The automated biological sample dispensing apparatus according to claim 1, wherein the chip accommodating section comprises a sending part for supplying the accommodated pipette chips to the conveying section; and
    the static eliminator removes the electrification charge of the pipette chips positioned at the sending part or the conveying section.

4. The automated biological sample dispensing apparatus according to claim 3, wherein the conveying section comprises a conveying path for conveying the pipette chips supplied from the sending part, a sorter for sorting one by one the pipette chips received from the conveying path, and a transfer section for transferring the pipette chip so that the distal end of the pipette chip faces downward.

5. The automated biological sample dispensing apparatus according to claim 1, wherein the static eliminator comprises a fan for blowing ionized air.

6. The automated biological sample dispensing apparatus according to claim 5, wherein the chip accommodating section has an opening for supplying the accommodating pipette chips to the conveying section; and the fan blows the ionized air toward the opening.

7. The automated biological sample dispensing apparatus according to claim 1, wherein the static eliminator comprises a conductive member for removing electrification charge of the pipette chips by contacting the pipette chips.

8. The automated biological sample dispensing apparatus according to claim 7, wherein the conductive member is a conductive brush.

9. The automated biological sample dispensing apparatus according to claim 8, wherein the conveying section comprises a transfer section for transferring the pipette chip so that the distal end of the pipette chip faces downward; and
    the conductive brush is arranged so as to contact the pipette chips transferred by the transfer section.

10. The automated biological sample dispensing apparatus according to claim 7, wherein the conductive member is a conductive sheet.

11. The automated biological sample dispensing apparatus according to claim 10, wherein the conveying section comprises a conveying path for conveying the pipette chips supplied from the chip accommodating section, a sorter for sorting one by one the pipette chips received from the conveying path, and a transfer section for transferring the pipette chip so that the distal end of the pipette chip faces downward; and the conductive sheet is arranged at the chip accommodating section, the conveying path, the sorter, or the transfer section.

12. The automated biological sample dispensing apparatus according to claim 1, wherein the conveying section comprises a transfer section for transferring one by one the pipette chips supplied from the chip accommodating section to the chip attaching position.

13. A sample analyzing apparatus comprising:
an automated biological sample dispensing apparatus according to claim 1; and
an analyzing section for analyzing the biological sample dispensed by the suction part automated biological sample dispensing apparatus.

14. An automated biological sample dispensing apparatus comprising:
a pipette chip supply device comprising
a chip accommodating section configured to accommodate the pipette chips,
a conveying path configured to convey the pipette chips supplied from the chip accommodating section,
a detector configured to detect the accumulation of the pipette chips in the conveying path,
a discharging section configured to discharge the accumulated pipette chips of the conveying path based on the detection of the accumulation by the detector,
a sorter configured to sort one by one the pipette chips received from the conveying path and
a transfer section configured to transfer the sorted pipette chip to a chip attaching position;
a container transport device configured to transport a container to a dispensing position; and
a sample dispense device configured to attach the transferred pipette chip at the chip attaching position and to dispense a biological sample to the transported container at the dispensing position by using the attached pipette chip,
wherein the transfer section comprises
a first shaft and
a rotatable feed screw arranged in parallel to the first shaft at a predetermined distance, the first shaft and the feed screw being configured to hold the sorted pipette chip and to transfer the sorted pipette chin by rotation of the feed screw;
wherein the sample dispensing device comprises
a second shaft,
an arm part connected to the second shaft and having a nozzle which is configured to attach a pipette chip, and
a motor for turning the arm part through the second shaft.

15. The automated biological sample dispensing apparatus according to claim 14, wherein the conveying path comprises an inclined path for conveying the pipette chips from the chip accommodating section; and
the discharging section discharges the pipette chips from a discharging opening.

16. The automated biological sample dispensing apparatus according to claim 15, wherein the discharging opening is opened by changing the angle of the inclined path.

17. The automated biological sample dispensing apparatus according to claim 14; wherein
the transfer section transfers the sorted pipette chip so that the distal end of the pipette chip faces downward.

18. The automated biological sample dispensing apparatus according to claim 14, wherein the chip accommodating section comprises a chip accommodating room for accommodating pipette chips, and a sending part for supplying a predetermined amount of pipette chips accommodated in the chip accommodating room to the conveying path.

19. The automated biological sample dispensing apparatus according to claim 18, further comprising a resupply section for returning the pipette chips discharged by the discharging section to the chip accommodating room.

20. A sample analyzing apparatus comprising:
an automated biological sample dispensing apparatus according to claim 14; and
an analyzing section for analyzing the biological sample dispensed by the automated biological sample dispensing apparatus.

21. An automated biological sample dispensing apparatus comprising:
a pipette chip supply device comprising
a chip accommodating section configured to accommodate pipette chips,
a sending part configured to supply pipette chips accommodated in the chip accommodating section,
a conveying path configured to convey the pipette chips sent from the sending part,
a supply section configured to supply one by one the pipette chips received from the conveying path to a chip attaching position,
a chip detector configured to detect the pipette chip in the conveying path and
a sending controller configured to control the sending part such that the sending part stops to supply the pipette chips to the conveying part when the chip detector detects the pipette chip;
a container transport device configured to transport a container to a dispensing position; and
a sample dispense device configured to attach the transferred pipette chips at the chip attaching position and to dispense a biological sample to the transported container at the dispensing position by using the attached pipette chip,
wherein the supply section comprises
a first shaft and
a rotatable feed screw arranged in parallel to the first shaft at a predetermined distance, the first shalt and the feed screw being configured to hold the conveyed pipette chip and to transfer the conveyed pipette chip by rotation of the feed screw,
wherein the sample dispense device comprises
a second shaft,
an arm part connected to the second shaft and having a nozzle which is configured to attach a pipette chip, and
a motor for turning the arm part through the second shaft.

22. The automated biological sample dispensing apparatus according to claim 21, wherein the supply section comprises a sorter for sorting one by one the pipette chips received from the conveying path and a transfer section for transferring the pipette chips so that the distal end of the sorted pipette chips faces downward.

23. A sample analyzing apparatus comprising:
an automated biological sample dispensing apparatus according to claim 21; and
an analyzing section for analyzing the biological sample dispensed by the automated biological sample dispensing apparatus.

24. An automated biological sample dispensing apparatus comprising:
- a pipette chip supply device comprising
  - a chip accommodating section configured to accommodate pipette chips,
  - a sending part configured to supply pipette chips accommodated from the chip accommodating section,
  - a sorter configured to sort one by one the pipette chips sent from the sending part,
  - a transfer section configured to transfer the pipette chip to a chip attaching position so that the distal end of the sorted pipette chip faces downward,
  - a first chip detector configured to detect whether the pipette chip is supplied from the sorter to the transfer section,
  - a second chip detector configured to detect whether the pipette chip is discharged from the transfer section, and
  - a controller configured to control the sorter so as to sort the pipette chips based on the first and second chip detected results;
- a container transport device configured to transport a container to a dispensing position; and
- a sample dispense device configured to attach the transferred pipette chip at the chip attaching position and to dispense a biological sample to the transported container at the dispensing position by using the attached pipette chip, wherein the transfer section comprises
- a first shaft and
- a rotatable feed screw arranged in parallel to the first shaft at a predetermined distance the first shaft and the feed screw being configured to hold the sorted pipette chip and to transfer the sorted pipette chip by rotation of the feed screw, wherein the sample dispense device comprises
- a second shaft,
- an arm part connected to the second shaft and having a nozzle which is configured to attach to a pipette chip, and
- a motor for turning the arm part through the second shaft.

25. A sample analyzing apparatus comprising:
- an automated biological sample dispensing apparatus according to claim 24; and
- an analyzing section for analyzing the biological sample dispensed by the automated biological sample dispensing apparatus.

* * * * *